(12) United States Patent
Marr

(10) Patent No.: US 11,079,380 B2
(45) Date of Patent: Aug. 3, 2021

(54) OPTIMIZING DIAGNOSTICS FOR GALACTOFURANOSE CONTAINING ANTIGENS

(71) Applicant: The Johns Hopkins University, Baltimore, MD (US)

(72) Inventor: Kieren Marr, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 16/750,720

(22) Filed: Jan. 23, 2020

(65) Prior Publication Data

US 2020/0225224 A1   Jul. 16, 2020

Related U.S. Application Data

(63) Continuation of application No. 15/882,278, filed on Jan. 29, 2018, now Pat. No. 10,585,098, which is a continuation-in-part of application No. 14/546,830, filed on Nov. 18, 2014, now Pat. No. 9,915,657, which is a continuation of application No. 13/511,264, filed as application No. PCT/US2010/057819 on Nov. 23, 2010, now Pat. No. 10,288,611.

(60) Provisional application No. 61/263,498, filed on Nov. 23, 2009.

(51) Int. Cl.
```
G01N 33/53       (2006.01)
G01N 33/569      (2006.01)
C07K 16/14       (2006.01)
G01N 33/66       (2006.01)
G01N 33/543      (2006.01)
C07K 16/44       (2006.01)
```

(52) U.S. Cl.
CPC ....... *G01N 33/56961* (2013.01); *C07K 16/14* (2013.01); *C07K 16/44* (2013.01); *G01N 33/54366* (2013.01); *G01N 33/569* (2013.01); *G01N 33/56911* (2013.01); *G01N 33/66* (2013.01); *G01N 2400/02* (2013.01); *G01N 2469/10* (2013.01); *Y02A 50/30* (2018.01)

(58) Field of Classification Search
CPC ................................................ G01N 33/56961
See application file for complete search history.

(56) References Cited

U.S. PATENT DOCUMENTS

| | | |
|---|---|---|
| 4,943,522 A | 7/1990 | Eisinger et al. |
| 5,149,632 A | 9/1992 | Notermans et al. |
| 5,710,005 A | 1/1998 | Rittenburg |
| 5,766,961 A | 6/1998 | Pawlak et al. |
| 5,876,961 A | 3/1999 | Crowe et al. |
| 5,945,294 A | 8/1999 | Frank et al. |
| RE37,437 E | 11/2001 | Friesen et al. |
| 6,500,629 B1 | 12/2002 | Cleaver et al. |
| 7,097,983 B2 | 8/2006 | Markovsky et al. |
| 7,371,582 B2 | 5/2008 | Nahm et al. |
| 9,915,657 B2 | 3/2018 | Marr et al. |
| 10,288,611 B2 * | 5/2019 | Marr ................. G01N 33/56961 |
| 10,585,098 B2 * | 3/2020 | Marr ..................... C07K 16/44 |
| 2002/0045195 A1 | 4/2002 | Hubscher et al. |
| 2003/0082533 A1 | 5/2003 | Yue et al. |
| 2003/0124630 A1 | 7/2003 | Prince et al. |
| 2003/0148484 A1 | 8/2003 | Koentgen et al. |
| 2004/0018556 A1 | 1/2004 | Cantor |
| 2005/0042738 A1 | 2/2005 | Swarnakar et al. |
| 2005/0074410 A1 | 4/2005 | Crameri et al. |
| 2005/0214836 A1 | 9/2005 | Nakamura et al. |
| 2005/0214951 A1 | 9/2005 | Nahm et al. |
| 2005/0272106 A1 | 12/2005 | Moore et al. |
| 2006/0019406 A1 | 1/2006 | Wei et al. |
| 2006/0121626 A1 | 6/2006 | Imrich |
| 2006/0127886 A1 | 6/2006 | Kaylor et al. |
| 2006/0134608 A1 | 6/2006 | Guo et al. |
| 2006/0148102 A1 | 7/2006 | Guo et al. |

(Continued)

FOREIGN PATENT DOCUMENTS

| | | |
|---|---|---|
| EP | 0325004 A1 | 7/1989 |
| EP | 0325004 B1 | 3/1993 |

(Continued)

OTHER PUBLICATIONS

Nielsen et al., "Prototype single step lateral flow technology for detection of avian influenza virus and chicken antibody to avian influenza virus." J Immunoassay Immunochem, 2007.28(4): p. 307-18.

(Continued)

*Primary Examiner* — Albert M Navarro
(74) *Attorney, Agent, or Firm* — Mintz Levin Cohn Ferris Glovsky and Popeo, P.C.; Peter F. Corless

(57) ABSTRACT

Disclosed herein are methods of detecting microbial infection in mammalian subjects comprising treatment of a sample and detection of galactofuranose (galF)-containing antigenic components utilizing monoclonal antibodies. The methods disclosed provide for pretreatment of biological samples, such as urine samples, to maximize detection of galF antigens and improvement of sensitivity of galF antigen detection assays. The methods include minimizing intelectin-1 binding to galF antigens and improvement of monoclonal antibody binding. The detection methods are useful for identifying the presence of microbial antigens related to bacterial, fungal, and parasitic pathogens, including *Streptococcus pneumoniae*, *Aspergillus* species, *Fusarium* species, *Coccidioides* species, *Cryptococcus* species, *Histoplasma* species, and *Leishmania* species.

11 Claims, 14 Drawing Sheets

(8 of 14 Drawing Sheet(s) Filed in Color)

Specification includes a Sequence Listing.

(56) References Cited

U.S. PATENT DOCUMENTS

| | | |
|---|---|---|
| 2006/0241288 A1 | 10/2006 | Roche et al. |
| 2007/0020711 A1 | 1/2007 | Wheat |
| 2008/0147031 A1 | 6/2008 | Long et al. |
| 2009/0117585 A1 | 5/2009 | Van Den Hondel |
| 2010/0119533 A1 | 5/2010 | Clancy et al. |
| 2010/0168023 A1 | 7/2010 | Ruegg et al. |
| 2011/0177532 A1 | 7/2011 | Rubin-Bejerano et al. |
| 2012/0015361 A1 | 1/2012 | Biro et al. |
| 2012/0064093 A1 | 3/2012 | Thornton |
| 2013/0017561 A1 | 1/2013 | Marr et al. |
| 2013/0130274 A1 | 5/2013 | Kelly |
| 2014/0178884 A1 | 6/2014 | Aucoin et al. |
| 2014/0212436 A1 | 7/2014 | Moore et al. |
| 2014/0303012 A1 | 10/2014 | Alocilja et al. |
| 2016/0053009 A1 | 2/2016 | Peterson et al. |
| 2016/0131649 A1 | 5/2016 | Kiessling et al. |

FOREIGN PATENT DOCUMENTS

| | | |
|---|---|---|
| EP | 1104768 A1 | 6/2001 |
| WO | 2007011221 A2 | 1/2007 |
| WO | 2007015177 A2 | 2/2007 |
| WO | 2007011221 A3 | 3/2007 |
| WO | 2010082034 A1 | 7/2010 |

OTHER PUBLICATIONS

Suarez et al., "Detection of circulating Aspergillus fumigatus DNA by real-time PCR assay of large serum volumes improves early diagnosis of invasive aspergillosis in high-risk adult patients under hematologic surveillance." J Clin Microbial, 2008. 46(11): p. 3772-7.

Cuenca-Estrella et al., "Value of serial quantification of fungal DNA by a real-time PCR-based technique for early diagnosis of invasive Aspergillosis in patients with febrile neutropenia." J Clin Microbiol, 2009. 47(2): p. 379-84.

Costa et al., "Development of two real-time quantitative TaqMan PCR assays to detect circulating Aspergillus fumigatus DNA in serum," J Microbiol Methods, 2001. 44(3): p. 263-9.

Costa et al., "Real-Time PCR Coupled with Automated DNA Extraction and Detection of Galactomannan Antigen in Serum by Enzyme-Linked Immunosorbent Assay for Diagnosis of Invasive Aspergillosis." J Clin Microbiol, 2002. 40(6): p. 2224-2227.

Kami et al., "Use of real-time PCR on blood samples for diagnosis of invasive aspergillosis." Clin Infect Dis, 2001. 33(9): p. 1504-12.

Hebart et al., "Early detection of aspergillus infection after allogeneic stem cell transplantation polymerase chain reaction screening." J Infect Dis, 2000. 181(5): p. 1713-9.

Van Burik et al., "Panfungal PCR assay for detection of fungal infection in human blood samples." J Clin Microbiol, 1998. 36(5): p. 1169-1175.

Clarke, "Urinary antigen diagnosis of meningococcal disease." Br J Biomed Sci, 2000. 57(2): p. 153-5.

Sutherland et al., "In vivo fate and distribution of poly-gamma-D-glutamic acid, the capsular antigen from Bacillus anthracis." Infect Immun, 2008. 76(3): p. 899-906.

Boulware et al., "Rapid diagnosis of pneumococcal pneumonia among HIVinfected adults with urine antigen detection." J Infect, 2007. 55(4): p. 300-9.

Ellis et al., "Assessment of the clinical utility of serial beta-D-glucan concentrations in patients with persistent neutropenic fever." J Med Microbiol, 2008. 57(Pt 3): p. 287-95.

Pickering et al., "Evaluation of a (1-43)-beta-D-glucan assay for diagnosis of invasive fungal infections." J Clin Microbiol, 2005. 43(12): p. 5957-62.

Persat et al., "Contribution of the (1-43)-beta-D-glucan assay for diagnosis of invasive fungal infections." J Clin Microbiol, 2008. 46(3): p. 1009-13.

Senn et al., "1,3-Beta-D-glucan antigenemia for early diagnosis of invasive fungal infections in neutropenic patients with acute leukemia." Clin Infect Dis, 2008. 46(6): p. 878-85.

Hachem et al., "Utility of galactomannan enzyme immunoassay and (1.3) beta-D-glucan in diagnosis of invasive fungal infections: low sensitivity for Aspergillus fumigatus infection in hematologic malignancy patients." J Clin Microbiol, 2009. 47(1): p. 129-33.

Steele et al., "The beta-glucan receptor dectin-1 recognizes specific morphologies of Aspergillus fumigatus." PLoS Pathog, 2005. 1(4): p. e42.

Hohl et al., "Aspergillus fumigatus triggers inflammatory responses by stagespecific beta-glucan display." PLoS Pathog, 2005. 1(3): p. e30.

Gersuk et al., "Dectin-1 and TLRs permit macrophages to distinguish between different Aspergillus fumigatus cellular states." J Immunol, 2006. 176(6): p. 3717-24.

Obayashi et al., "Plasma (1→3)-beta-D-glucan measurement in diagnosis of invasive deep mycosis and fungal febrile episodes." Lancet, 1995. 345(8941): p. 17-20.

Tsoni et al., "beta-Glucans and dectin-1." Ann N Y Acad Sci, 2008. 1143: p. 45-60.

Rogers et al., "Value of antigen detection in predicting invasive pulmonary aspergillosis." Lancet, 1990. 336(8725): p. 1210-3.

Dupont et al., "Galactomannan antigenemia and antigenemia in aspergillosis: studies in patients and experimentally infected rabbits." J Infect Dis, 1987. 155(1): p. 1-11.

Ansorg et al., "Aspergillus antigenuria compared to antigenemia in bone marrow transplant recipients." Eur J Clin Microbiol Infect Dis, 1994. 13(7): p. 582-9.

Klont et al., "Utility of Aspergillus antigen detection in specimens other than serum specimens." Clin Infect Dis, 2004. 39(10): p. 1467-74.

Bennett et al., "Receptor-mediated clearance of Aspergillus galactomannan." J Infect Dis, 1987. 155(5): p. 1005-10.

Jensen et al., "Detection of galactomannan and the 18 kDa antigen from Aspergillus fumigatus in serum and urine from cattle with systemic aspergillosis." Zentralbl Veterinarmed [B], 1993. 40(6): p. 397-408.

Becker et al., "Galactomannan detection in computerized tomography-based broncho-alveolar lavage fluid and serum in haematological patients at risk for invasive pulmonary aspergillosis." Br J Haematol, 2003. 121(3): p. 448-57.

Sanguinetti et al., "Comparison of real-time PCR, conventional PCR, and galactomannan antigen detection by enzyme-linked immunosorbent assay using bronchoalveolar lavage fluid samples from hematology patients for diagnosis of invasive pulmonary aspergillosis." J Clin Microbiol, 2003. 41(8): p. 3922-5.

Clancy et al., "Bronchoalveolar lavage galactomannan in diagnosis of invasive pulmonary aspergillosis among solid-organ transplant recipients." J Clin Microbiol, 2007. 45(6): p. 1759-65.

Husain et al., "Aspergillus galactomannan antigen in the bronchoalveolar lavage fluid for the diagnosis of invasive aspergillosis in lung transplant recipients." Transplantation, 2007. 83(10): p. 1330-6.

Nguyen et al., "Use of bronchoalveolar lavage to detect galactomannan for diagnosis of pulmonary aspergillosis among nonimmunocompromised hosts." J Clin Microbiol, 2007. 45(9): p. 2787-92.

Husain et al., "Performance characteristics of the platelia Aspergillus enzyme immunoassay for detection of Aspergillus galactomannan antigen in bronchoalveolar lavage fluid." Clin Vaccine Immunol, 2008. 15(12): p. 1760-3.

Meersseman et al., "Galactomannan in bronchoalveolar lavage fluid: a tool for diagnosing aspergillosis in intensive care unit patients." Am J Respir Crit Care Med, 2008. 177(1): p. 27-34.

Buchheidt et al., "Detection of Aspergillus species in blood and bronchoalvolar lavage samples from immunocompromised patients by means of 2-step polymerase chain reaction: clinical results." Clin Infect Dis, 2001. 33: p. 428-35.

Einsele et al., "Prediction of invasive pulmonary aspergillosis from colonisation of lower respiratory tract before marrow transplantation." Lancet, 1998. 352(9138): p. 1443.

(56) References Cited

OTHER PUBLICATIONS

Eskens et al., "Septic shock caused by group G beta-haemolytic streptococci as presenting symptom of acute myeloid leukaemia." Neth J Med, 1995. 46(3): p. 153-5.
Rath et al., "Value of environmental sampling and molecular typing of aspergilli to assess nosocomial sources of aspergillosis." J Hosp Infect, 1997. 37(1): p. 47-53.
Maertens et al., "Optimization of the cutoff value for the Aspergillus doublesandwich enzyme immunoassay." Clin Infect Dis, 2007. 44(10): p. 1329-36.
Denning et al., "Efficacy and safety of voriconazole in the treatment of acute invasive aspergillosis." Clin Infect Dis, 2002. 34(5): p. 563-71.
Stynen et al., "Rat monoclonal antibodies against Aspergillus galactomannan." Infect Immun, 1992. 60(6): p. 2237-45.
Musher et al., "Aspergillus galactomannan enzyme immunoassay and quantitative PCR for diagnosis of invasive aspergillosis with bronchoalveolar lavage fluid." J Clin Microbiol, 2004. 42(12): p. 5517-22.
Marr et al., "Antifungal therapy decreases sensitivity of the Aspergillus galactomannan enzyme immunoassay." Clin Infect Dis, 2005. 40(12): p. 1762-9.
Marr et al., "Design issues in studies evaluating diagnostic tests for aspergillosis." Clin Infect Dis, 2005.41 Suppl 6: p. S381-6.
Upton et al., "(1→3) beta-D-glucan assay in the diagnosis of invasive fungal infections." Clin Infect Dis, 2006. 42(7): p. 1054-6; author reply 1056.
Sheppard et al., "Comparison of three methodologies for the determination of pulmonary fungal burden in experimental murine aspergillosis." Clin Microbiol Infect 2006. 12(4): p. 376-80.
Marr, "Aspergillus galactomannan index: a surrogate end point to assess outcome of therapy?" Clin Infect Dis, 2008. 46(9): p. 1423-5.
Upton et al., "Reproducibility of low galactomannan enzyme immunoassay index values in multiple laboratories." in preparation, 2005.
Marr et al., "Detection of galactomannan antigenemia by enzyme immunoassay for the diagnosis of invasive aspergillosis: variables that affect performance." J Infect Dis, 2004. 190(3): p. 641-9.
De Sevaux et al., "Microgranulomatous aspergillosis in a patient with chronic granulomatous disease: cure with voriconazole." Clin Infect Dis, 1998. 26(4): p. 996-7.
Rogers, T. R. et al, 1990, Value of antigen detection in predicting invasive pulmonary aspergillus, Lancet, vol. 336, pp. 1210-1213.
Hurst, Steven F. et al, Clinical and Diagnostic Laboratory Immunology, May 2000, pp. 477-485, vol. 7(3), Comparison of Commercial Latex Agglutination and Sandwich Enzyme Immunoassays with a Competitive Binding Inhibition Enzyme Immunoassay for Detection of Antigenemia and Antigenuria in a Rabbit Model of Invasive Aspergillosis.
Latge, Jean-Paul et al., Infection and Immunity, vol. 62(12), Dec. 1994, pp. 5424-5433, Chemical and Immunological Characterization of the Extracellular Galactomannan of Aspergillus fumigatus.
Leitao, E. A. et al, Glycobiology, vol. 13(10), pp. 681-692, 2003, B-Galactofuranose-containing O-linked oligosaccharides present in cell wall peptidogalactomannan of Aspergillus fumigatus contain immunodominant epitopes.
Sarfati, J et al, Journal of Medical and VEterinary Mycology, 1995, vol. 33, pp. 9-14, Antigens of Aspergillus fumigatus produced in vivo.
Latge, Jean-Paul, Medical Mycology, 2009, vol. 47(supplement 1), pp. S104-S109, Galactofuranose containing molecules in Aspergillus fumigatus.
Anastasakou, E et al, ECCMID, 9th, Aspergillus and Aspergillosis Website, Ref. ID 2970, year 1999, abstract, Detection of antigen galactomannan of Aspergillus in the urine of patients with lung disease.
Suzuki, E. et al, Clinical and Diagnostic Laboratory Immunology, Sep. 2001, vol. 8(5), pp. 1031-1035, Reactivity of MEST-1 (Antigalactofuranose) with Trypanosoma cruzi Glycosylinositor Phosphorylceramides (GIPCs): Immunolocalization of GIPCs in Acidic Vesicles of Epimastigotes.

Mennink-Keisten, Monique A.S. et al, Journal of Clinical Microbiology, May 2006, pp. 1711-1718, vol. 44(5), In Vitro Release by Aspergillus fumigatus of Galactofuranose Antigens, 1, 3-B-D-Glucan, and DNA, Surrogate Markers Used for Diagnosis of Invasive Aspergillosis.
Stynen, Dirk et al, Infection and Immunity, vol. 60(6), Jun. 1992, pp. 2237-2245, Rat Monoclonal antibodes against Aspergillus Galactomannan.
Christopher R. Thornton, Clinical and Vaccine Immunology, vol. 15(y), Jul. 2008, pp. 1095-1105, Development of an Immunochromatographic Lateral Flow Device for Rapid Serodiagnosis of Invasive Aspergillosis.
Ohta, M. et al, Bioscience, Biotechnology and Biochemistry, Novel B-D-Galactofuranose-containing High Mannose Type Oligosaccharides in Ascorbate Oxidase from *Acremonium* sp. HI-25, vol. 60(7), pp. 1123-1130, 1996.
Response and Amendment filed Nov. 14, 2014 in Response to Office Action dated Oct. 20, 2014 in related case U.S. Appl. No. 13/511,264.
Response and Amendment and 1.132 Declaration filed Feb. 10, 2015 in Response to Final Office Action dated Jan. 14, 2015 in related case U.S. Appl. No. 13/511,264.
Response and Amendment and 1.132 Declarations filed May 6, 2015 in Response to Final Office Action dated Mar. 24, 2015 in related case U.S. Appl. No. 13/511,264.
Office Action dated Jul. 24, 2015 in related case U.S. Appl. No. 13/511,264.
Advisory Action dated Feb. 20, 2015 in related case U.S. Appl. No. 13/511,264.
USPTO After Final Program Consideration Decision on After Final Consideration Program Request filed Feb. 10, 2015 in related case U.S. Appl. No. 13/511,264.
Office Action dated Oct. 20, 2014 for U.S. Appl. No. 13/511,264.
Final Office Action dated Jan. 14, 2015 for U.S. Appl. No. 13/511,264.
Thornton, C., "Development of an immunochromatographic lateralflow device for rapid serodiagnosis of invasive aspergillosis", Clinical and Vaccine Immunology, Jul. 2008, vol. 15, No. 7, pp. 1095-1105.
Office Action dated Mar. 24, 2015 for U.S. Appl. No. 13/511,264.
Kamphuis, HJ, 1992, Ph.D. Thesis, Wageningen Agricultural University, pp. 1-157 (provided in three separate parts), Extracelluar polysaccharides as target Compounds for the Immunological Detection of Aspergillus and Penicillium in Food, Chapters 1-9, Agricultural University Wageningen, Netherlands.
Dupont, Bertrand et al, The Journal of Infectious Diseases, vol. 155(1) Jan. 1, 1987, pp. 1-1, Galactomannan Antigenemia and Antigenuria in Aspergillus: Studies in Patients and Experimentally Infected Rabbits.
Wiederhold, Nathan P. et al, Clinical and Vaccine Immunology, Dec. 2009, published on line ahead of print Sep. 30, 2009, pp. 1844-1846, vol. 16(12), Comparison of Lateral Flow Technology and Galactomannan and (1>3)-B-D-Glucan Assays for Detection of Invasive Pulmonary Aspergillus.
Klont, RR et al, Clinical Infectious Diseases, 2004, vol. 39, pp. 1467-1474, Utility of Aspergillus Antigen Detection in Specimens other than Serum Specimens.
Notice of Appeal, Pre-Appeal Brief Request for Review, and Reasons for Review dated Apr. 26, 2016, in Response to Final Office Action dated Mar. 21, 2016, in related case U.S. Appl. No. 13/511,264.
Appeal Brief filed Jul. 15, 2016, in related case U.S. Appl. No. 13/511,264.
Domenech, J. et al., "Galactomannans from the cell walls of species of Paeci lomyces sect. Paecilomyces and their telemorphs as immunotaxonomic markers" Microbiology, 1999, vol. 145. pp. 2789-2796.
Leisenring et al., "A marginal regression modelling framework for evaluation medical diagnostic tests." Statistics in Medicine, 1997. 16(11): p. 1263-1281.
Sheppard et al., "Novel inhalational murine model of invasive pulmonary aspergillosis." Antimicrob Agents Chemother, 2004. 48(5): p. 1901-11.
Sheppard et al., "Standardization of an experimental murine model of invasive pulmonary aspergillosis." Antimicrob Agents Chemother, 2006. 50(10): p. 3501-3.

(56) References Cited

OTHER PUBLICATIONS

Stynen et al., "A New Sensitive Sandwich Enzyme-Linked Immunosorbent Assay to Detec Galactofuran in patients with Invasive Aspergillosis," J. Clin. Micro., vol. 33, No. 2, Feb. 1995, pp. 497-500.
Hurst et al., "Comparison of Commercial Latex Agglutination and Sandwith Enzyme Immunoassays wiht a Competitive Binding Inhibition Enzyme Immunoassay for Detection of Antigenemia and Antigenuria in a Rabbit Model of Invasive Aspergillosis," Clin. Diag. Lab. Immun., vol. 7, No. 3, May 2000, pp. 477-485.
Salonen et al., "Aspergillus antigen in serum, using and broncholaveolar lavage speciments of neutropenic patients in relation to clinical outcome," Scandinavian Journal of Infectious Diseases, 2000, 32, pp. 485-490.
Thornton, "Development of an immunochromatographic lateral-flow device for rapid serodiagnosis of invasive aspergillosis," Clin Vaccine Immunol, 2008. 15(7): p. 1095-105.
Ascioglu et al., "Defining opportunistic invasive fungal infections in immunocompromised patients with cancer and hematopoietic stem cell transplants: an international consensus." Clin. Infect Dis, 2002. 34: p. 7-14.
Khot et al., "Development and optimization of quantitative PCR for the diagnosis of invasive aspergillosis with bronchoalveolar lavage fluid." BMC Infect Dis, 2008. 8: p. 73.
Fredricks et al., "Comparison of six DNA extraction methods for recovery of fungal DNA as assessed by quantitative PCR." J Clin Microbial, 2005. 43(10): p. 5122-8.
Dalle et al., "Cryptococcus neoformans Galactoxylomannan contains an epitope(s) that is cross-reactive with Aspergillus Galactomannan." J Clin Microbial, 2005. 43(6): p. 2929-31.
Brown, Antibodies: key to a robust lateral flow immunoassay, in Lateral Flow Immunoassay, H.Y.T.R.C. Wong, Editor. 2009, Humana Press: New York, N.Y. p. 59-74.
Mennink-Kersten et al., "Bifidobacterium lipoteichoic acid and false ELISA reactivity in aspergillus antigen detection." Lancet, 2004. 363(9405): p. 325-7.
Walsh et al., "Experimental pulmonary aspergillosis due to Aspergillus terreus: pathogenesis and treatment of an emerging fungal pathogen resistant to amphotericin B" J Infect Dis, 2003. 188(2): p. 305-19.
Marr et al., "Antifungal therapy decreases sensitivity of the Platelia Aspergillus galactomannan enzyme immunoassay." submitted, 2005.
Swanink et al., "Specificity of a sandwich enzyme-linked immunosorbent assay for detecting Aspergillus galactomannan." J Clin Microbial, 1997. 35(1): p. 257-60.
Kappe et al., "New cause for false-positive results with the Pastorex Aspergillus antigen latex agglutination test." J Clin Microbial, 1993. 31(9): p. 2489-90.
Weatherall et al., "Point-of-care urinary pneumococcal antigen less in the emergency department for community acquired pneumonia." Emerg Med J, 2008. 25(3): p. 144-8.
Roson et al., "Contribution of a urinary antigen assay (Binax NOW) to the early diagnosis of pneumococcal pneumonia." Clin Infect Dis, 2004. 38(2): p. 222-6.
Koide et al., "Comparative evaluation of Duopath Legionella lateral flow assay against the conventional culture method using Legionella pneumophila and Legionella anisa strains." Jpn J Infect Dis, 2007. 60(4): p. 214-6.
Mokkapati et al., "Evaluation of UPlink-RSV: prototype rapid antigen test for detection of respiratory syncytial virus injection." Ann NY Acad Sci, 2007. 1098: p. 476-85.
A. Paugam et al., Journal of Clinical Microbiology, 36(10), pp. 3079-3080 (Oct. 1998).
K. Marino et al., Arkivoc, 2005 (xii), pp. 341-351.
R. Horler et al., The Journal of Biological Chemistry, 284(45), pp. 31156-31163 (Nov. 6, 2009).
S. Notermans et al., Molecular Immunology, 25(10), pp. 975-979 (1988).
JE Bennett et al., Molecular Immunology, 22(3), pp. 251-254 (1985).
PS Schmalhorst et al., Eukaryotic Cell, 7(8), pp. 1268-1277 (Aug. 2008).
Hoffer et al., "Accuracy of percutaneous lung biopsy for invasive pulmonary aspergillosis." Pediatr Radio!, 2001. 31(3): p. 144-52.
Levy et al., "The value of bronchoalveolar lavage and bronchial washings in the diagnosis of invasive pulmonary aspergillosis." Respir Med, 1992. 86(3): p. 243-8.
Caillot et al., "Improved management of invasive aspergillosis in neutropenic patients using early thoracic computed tomographic scan and surgery." Journal of Clinical Oncology, 1997. 15(1): p. 139-147.
Kim et al., "Halo sign on high resolution CT: findings in spectrum of pulmonary diseases with pathologic correlation." J Comput Assist Tomogr, 1999. 23(4): p. 622-6.
Spector et al., "Antigen and antibody testing for the diagnosis of blastomycosis in dogs." J Vet Intern Med, 2008. 22(4): p. 839-43.
Durkin et al., "Diagnosis of coccidioidomycosis with use of the Coccidioides antigen enzyme immunoassay." Clin Infect Dis, 2008. 47(8): p. e69-73.
Neofytos et al., "Epidemiology and outcome of invasive fungal infection in adult hematopoietic stem cell transplant recipients: analysis of Multicenter Prospective Antifungal Therapy (PATH) Alliance registry." Clin Infect Dis, 2009. 48(3): p. 265-73.
Wald et al., "Epidemiology of Aspergillus infections in a large cohort of patients undergoing bone marrow transplantation." The Journal of Infectious Diseases, 1997. 175: p. 1459-6.
Marr et al., "Epidemiology and outcome of mould infections in hematopoietic stem cell transplant recipients." Clin Infect Dis, 2002. 34: p. 909-917.
Hansen et al., "Bone marrow transplants from unrelated donors for patients with chronic myeloid leukemia." The New ngland Journal of Medicine, 1998. 338: p. 962-8.
Slavin et al., "Efficacy and safety of fluconazole prophylaxis for fungal infections after marrow transplantation—a prospective, randomized, double-blind study." Journal of Infectious Diseases., 1995. 171(6): p. 1545-52.
Boeckh et al., "Cytomegalovirus pp65 antigenemia-guided early treatment with ganciclovir versus ganciclovir at engraftment after allogeniec marrow transplantation: a randomized double-blind study." Blood, 1996. 88(10): p. 4063-4071.
Boeckh et al., "Plasma polymerase chain reaction for cytomegalovirus DNA after allogeneic marrow transplantation: comparison with polymerase chain reaction using peripheral blood leukocytes, pp65 antigenemia, and viral culture." Transplantation, 1997. 64: p. 108-113.
Boeckh et al., "Effect of high-dose acyclovir on survival in allogeneic marrow transplant recipients who received ganciclovir at engraftment or for cytomegalovirus pp65 antigenemia." J Infect Dis, 1998. 1998(178): p. 1153-7.
Boeckh et al., "Successful modification of a pp65 antigenemia-based early treatment strategy for prevention of cytomegalovirus disease in allogeneic marrow transplant recipients." Blood, 1999. 93(5): p. 1781-2.
Marr et al., "Aspergillosis in HSCT recipients: evidence for two distinct pathophysiologic conditions associated with engraftment status" Blood, 2000. 96(11).
Berenguer et al., "Pathogenesis of pulmonary aspergillosis. Granulocytopenia versus cyclosporine and methylprednisolone-induced immunosuppression." Am J Respir Crit Care Med, 1995. 152(3): p. 1079-86.
Duong et al., "Kinetic study of host defense and inflammatory response to Aspergillus fumigatus in steroid-induced immunosuppressed mice." J Infect Dis, 1998. 178: p. 1472-82.
Khoo et al., "Invasive aspergillosis in patients with AIDS." Clin Infect Dis, 1994. 19 Suppl 1(2): p. S41-8.
Hines et al., "Pseudomembranous tracheobronchitis caused by Aspergillus." Am Rev Respir Dis, 1991. 143(6): p. 1408-11.
Staples et al., "Invasive pulmonary aspergillosis in AIDS: radiographic, CT, and pathologic findings" Radiology, 1995. 196(2): p. 409-14.
Wollschlager et al., "Aspergilloma complicating sarcoidosis. A prospective study of 100 patients." Chest, 1984. 86: p. 585-88.

(56) References Cited

OTHER PUBLICATIONS

Kirsten et al., "Invasive aspergillosis in cavitary lung sarcoidosis." Pneumologie, 1992. 46: p. 239-242.
Israel et al., "Sarcoidosis and aspergilloma" Chest, 1982. 82: p. 430-32.
Kawamura et al., "Clinical evaluation of 61 patients with pulmonary aspergilloma." Intern Med, 2000. 39(3): p. 209-12.
Knutsen et al., "Asp fl CD4+ Th2-like T cell lines in allergic bronchopulmonary aspergillosis." J Allergy Clin Immunol, 1994, 94: p. 215-221.
Schmalhorst et al (Eukaryot Cell. Aug. 2008; 7(8): 1268-77).
Greenspan et al (Nature Biotechnology 7: 936-937, 1999).
Chothia et al (The EMBO Journal, 1986, 5/4:823-26.
Thornton, CR (Clin Vaccine Immunol. Jul. 2008; 15(7): 1095-105.
Office Action dated Apr. 30, 2015 for U.S. Appl. No. 14/546,830.
Leitao, E. A. et al, Glycobiology, vol. 13(10), pp. 681-692, 2003, "B-Galactofuranose-containing 0-linked oligosaccharides present in cell wall peptidogalactomannan of Aspergillus fumigatus contain immunodominant epitopes".
Latgf, Jean-Paul el al, Infection and Immunity, vol. 62(12), Dec. 1994, pp. 5424-5433, "Chemical and Immunological Characterization of the Extracellular Galactomannan of Aspergillus fumigatus".
Suzuki, E. et al, Clinical and Diagnostic Laboratory Immunology, Sep. 2001, vol. 8(5), pp. 1031-1035, "Reactivity of MEST-1 (Antigalactofuranose) with Trypanosoma cruzi Glycosylinositol Phosphorylceramides (GIPCs): Immunolocalization of GIPCs in Acidic Vesicles of Epimastigotes".
Latge, Jean-Paul, "Galactofuranose containing molecules in Aspergillus fumigatus" Medical Mycology (2009) vol. 47 (supplement 1), pp. 8104-8109.
Sarfati, J et al, "Antigens of Aspergillus fumigatus produced in vivo" Journal of Medical and Veterinary Mycology (1995) vol. 33, pp. 9-14.
Masaya, C., et al, "Novel B-D-Galactofuranose-containing High Mannose Type Oligosaccharides in Ascorbate Oxidase from *Acremonium* sp HI-25", Bioscience, Biotechnology and Biochemistry (1996) vol. 60, No. 7, pp. 1123-1130.
Response and Amendment filed Apr. 22, 2016, in Response to Final Office Action dated Feb. 23, 2016 in related case U.S. Appl. No. 14/546,830.
Response and Amendment and 1.132 Declarations filed Jun. 11, 2015 in Response to Office Action dated Apr. 30, 2015 in related case U.S. Appl. No. 14/546,830.
Supplemental Response filed Jul. 8, 2016 in Response to Final Office Action dated Feb. 23, 2016, in related case U.S. Appl. No. 14/546,830.
Final Office Action dated Feb. 24, 2016 in related U.S. Appl. No. 14/546,830.
Tsuji et al., The Journal of Biological Chemistry, 276(26) pp. 23456-23463 (Jun. 29, 2001).
Fu et al., Carbohydrate Research, vol. 340, pp. 25-30 (2005).
Maetens et al., Aspergillosis: From Diagnosis to Prevention, pp. 105-124 (2010)—Galactomannan Testing.
Bretagne et al., Clinical Infectious Disease, vol. 26, pp. 1407-1412 (1998).
N.P. Wiederhold et al., Clinical and Vaccine Immunology, 16(12), pp. 1844-1846 (Dec. 2009).
E. Reiss et al., Medical Mycology, vol. 38, pp. 147-149 (2000 Supplement 1).
A. Sulahian et al., Cancer, vol. 91, pp. 311-318 (2001).
C. Costachel et al., The Journal of Biological Chemistry, 280(48), pp. 39835-39842 (Dec. 2, 2005).
Mennink-Kersten, Journal of Clinical Microbiology, pp. 1-28 (published Feb. 20, 2008).

\* cited by examiner

FIGURE 3

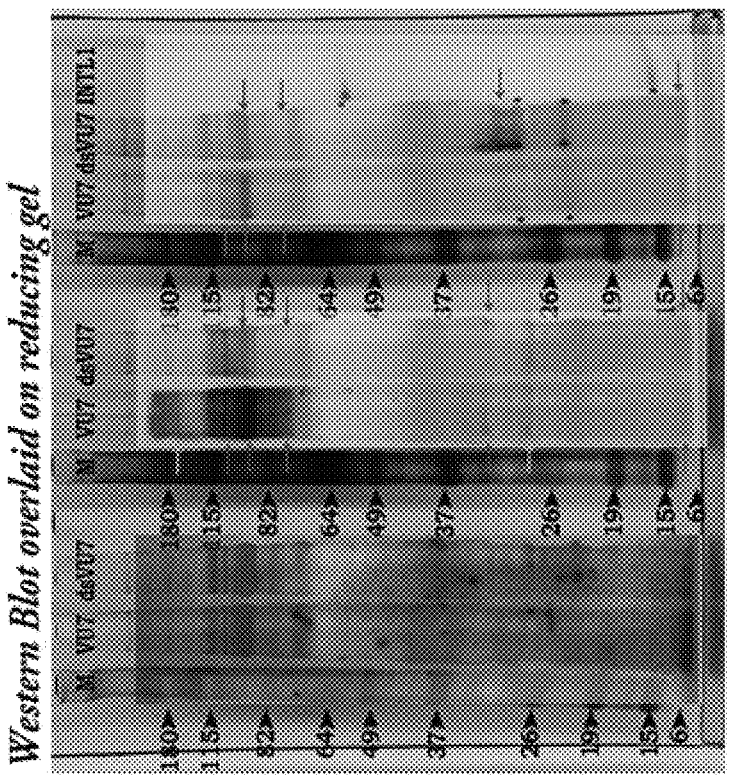
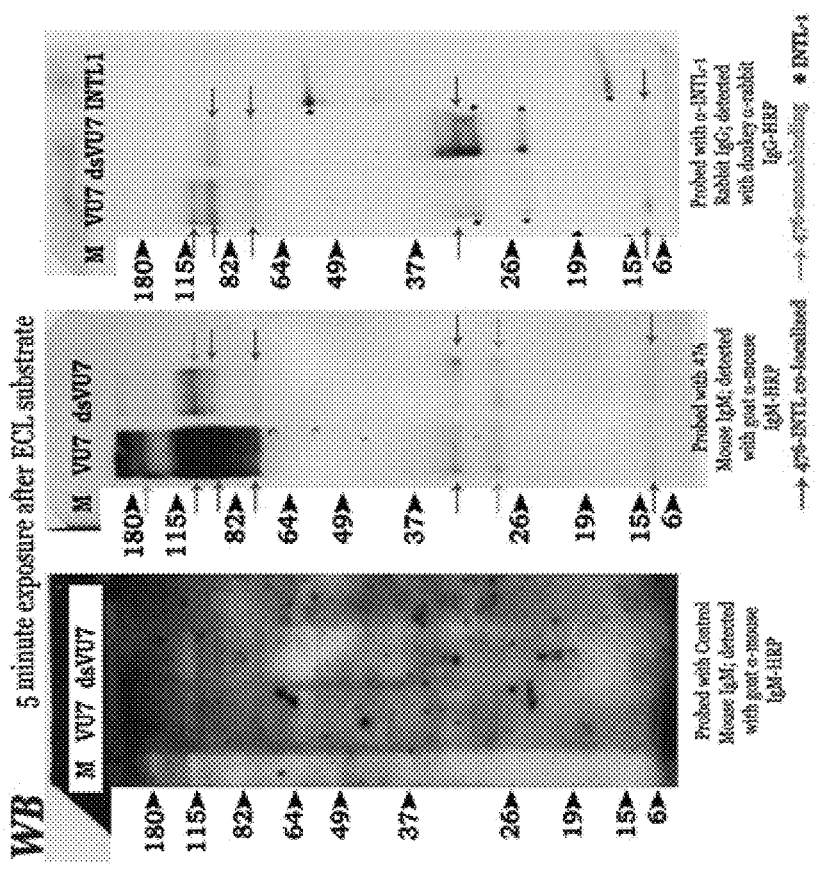
FIGURE 9

FIGURE 12

B    Mass Spec Analysis output

Via SCAFFOLD search

- hypothetical protein S165_03195 [Aspergillus cristatus] 140 a.a.

- BLAST search for this protein using non-redundant protein sequences (nr) and Aspergillus (taxid:5052) yields
  For *A. fumigatus* (first three results)
  XP_749833.1 allergen Asp F7-like [Aspergillus fumigatus Af293]
  GAQ07834.1 allergen Asp f7 [Aspergillus lentulus]
  XP_752159.1 allergen Asp F7 [Aspergillus fumigatus Af293]

CelA/Asp f7-like protein extracellular cellulase active in biofilms

- Looking for Af293 Asp F7 yields following accession numbers:
  XP_748682.1 glycosyl transferase [Aspergillus fumigatus Af293]
  XP_747137.1 glycosyl transferase [Aspergillus fumigatus Af293]
  EAL91795.1 extracellular cellulase CelA/allergen Asp F7-like, putative [Aspergillus fumigatus Af293]
  XP_753833.1 extracellular cellulase CelA/allergen Asp F7-like [Aspergillus fumigatus Af293]
  EAL85099.1 glycosyl transferase, putative [Aspergillus fumigatus Af293]
  EAL86644.1 glycosyl transferase, putative [Aspergillus fumigatus Af293]

- No N-glycosylation sites; several O-glycosylation sites (ExPASy and CBS)
  Expanding the search to include all Asparagine residues, provides two sites, which may be N-glycosylated.
  40 O-glycosylation sites predicted
  Interestingly, 3 mannosylation sites predicted (CBS)

PEAKS search to check for the possible presence of a single human protein

Sequences map to hIntL!

476-reactive material pulled down from dsVU7 contains hIntL

OPTIMIZING DIAGNOSTICS FOR GALACTOFURANOSE CONTAINING ANTIGENS

REFERENCE TO RELATED APPLICATIONS

This application is a continuation application of U.S. patent application Ser. No. 15/882,278, filed Jan. 29, 2018, which is a continuation-in-part application of U.S. patent application Ser. No. 14,546,830, filed on Nov. 18, 2014 which is a Continuation of U.S. patent application Ser. No. 13/511,264, filed on Sep. 25, 2012, which is a § 371 application of International Application No. PCT/US2010/057819, filed Nov. 23, 2010, which claims priority to U.S. Provisional Patent Application No. 61/263,498, filed Nov. 23, 2009, each of which are hereby incorporated by reference for all purposes as if fully set forth herein.

This invention was made with government support under grant numbers AI054736, AI053623, AI065745, awarded by the National Institutes of Health. The government has certain rights in the invention.

INCORPORATION-BY-REFERENCE OF MATERIAL SUBMITTED ELECTRONICALLY

The instant application contains a Sequence Listing which has been submitted in ASCII format via EFS-Web and is hereby incorporated by reference in its entirety. Said ASCII copy, created on Mar. 27, 2020, is named 048317-551C03US_SL.txt and is 6,931 bytes in size.

BACKGROUND OF THE INVENTION

Galactose is common in mammals, but only found in the 6-member ring hexopyranosyl form, called galactopyranose (galP). Galactofuranose (galF), the 5-member ring form of galactose, is found in other organisms, including bacteria, fungi, protozoa, lichens, green algae, starfish and sponges. Equilibrium strongly favors the galP form unless the organism contains specific enzymes to catalyze maintenance of galF. In these organisms, galF is an important residue on glycoconjugate antigens, and can be found linked to secreted and cellular polysaccharides, glycoproteins and glycosphingolipids. In certain organisms where the galF form is detected, introduction of galF is via inhalation and pulmonary introduction.

The present inventors previously identified a class of antibodies that were generated against conidia of an important fungal pathogen, called *Aspergillus fumigatus*. These antibodies were found to identify galF-containing antigens that were quickly excreted in urine after infection in mammals. The antibodies and the technology enable their use as a urine diagnostic assay.

What is needed however, are methods for improving detection and optimizing the sensitivity of the antibodies, namely improved detection of galF-containing antigens in biological samples such as urine. What is also needed are methods that improve sensitivity and performance of such detection assays with minimal sample processing.

SUMMARY OF THE INVENTION

In accordance with one or more embodiments, the present invention provides methods for improved galF antigen detection in human body fluids by disabling or otherwise removing a competitive inhibitor, the human lectin, intelectin-1 from the assay process previously disclosed in U.S. patent application Ser. No. 13/511,264, and incorporated by reference herein in its entirety. Although intelectin is known to be secreted by epithelial cells lining the GI tract and respiratory tract, and for recognizing galF antigens, intelectin was not known until now to be present in urine. The present inventors surprisingly determined that intelectin is also present in urine, and serves to compete with galF-directed antibodies when they are used as part of diagnosing microbial infections in a mammalian subject. Though not wishing to be bound by the following theory, it is thought that this inhibition or interference is dependent on calcium, which can be removed by chelation as a mechanism to optimize antigen identification.

In some embodiments, the microbial infection is caused by an organism selected from the group consisting of *Streptococcus pneumoniae*, *Aspergillus* species, *Fusarium* species, *Coccidioides* species, *Cryptococcus* species, and *Histoplasma* species.

In some embodiments, the microbial infection is caused by Prokaryotic and Eukaryotic pathogens that produce galF-containing antigens, including but not limited to, *Streptococcus* species, *Pseudomonas* species, *Nocardia* species, *Actinomyces* species. Zygomycetes and parasites, including but not limited to *Leishmania* species, and *Trypanosoma* species.

As such, in accordance with one or more embodiments, the present invention provides methods for optimization of galF-antigen identification in fluids that contain intelectin, including urine, respiratory fluids, gastrointestinal fluids, and blood. The present inventors found that this is important for optimizing those methods that specifically focus on fungal antigens. The utility is broadly applicable to diagnostics that target galF containing antigens in many different diagnostic systems, given the ubiquity of galF in microbial antigens.

In accordance with an embodiment, the present invention provides a method for diagnosing a microbial infection in a biological sample from a mammalian subject suspected of having, having, or susceptible to having a microbial infection by detecting the presence of at least one microbial molecule comprising a galactofuranose (galF) residue (for example, glycoprotein, polysaccharide or sphingolipid) in a biological sample of the mammalian subject, the method comprising: (a) treating the biological sample to decrease human intelectin (hIntL) binding of galF residues present in the sample; (b) allowing the treated sample of (a) to come in contact with at least one antibody specific for at least one molecule comprising a galF residue in an effective amount to produce a detectable amount of antibody-galF complex; and (c) detecting the presence of at least one antibody-galF complex, wherein the detection of the presence of at least one antibody-galF complex is diagnostic of a microbial infection in a mammalian subject.

In accordance with another embodiment, the present invention provides a method for diagnosing a microbial infection in a biological sample from a mammalian subject suspected of having, having, or susceptible to having a microbial infection by detecting the presence of at least one antigen comprising a galF residue in a biological sample of the mammalian subject, the method comprising: (a) treating the biological sample comprising contacting the sample with a substrate such as a ligand which binds directly to intelectin, or calcium or divalent cations with high affinity, thereby inhibiting or interfering with human intelectin (hIntL) binding of microbial molecule containing galF residues present in the sample; (b) contacting the treated sample of (a) with at least one antibody specific for at least one molecule comprising a galF residue in an effective amount to produce a detectable amount of antibody-galF complex; and (c) detecting the presence of at least one antibody-galF complex, wherein the detection of the presence of at least one antibody-galF complex is diagnostic of a microbial infection in a mammalian subject.

In accordance with some embodiments, the method for treating the sample in step (a) comprises contacting the sample with a substrate which binds $Ca^{2+}$ ions with high affinity.

In accordance with some embodiments, the method for treating the sample in step (a) comprises contacting the sample with a compound which chelates $Ca^{2+}$ ions with high affinity.

In accordance with some embodiments, the method for treating the sample in step (a) comprises contacting the sample with EDTA and/or EGTA.

In accordance with some embodiments, the method for treating the sample in step (a) comprises contacting the sample with a substrate which binds hIntL with high affinity.

In accordance with some embodiments, the method for treating the sample in step (a) comprises contacting the sample with an antibody specific for hIntL.

In accordance with some embodiments, the method for treating the sample in step (a) comprises contacting the sample with one or more compounds which are bound by hIntL with high affinity, thereby preventing galF-binding to hIntL.

In accordance with some embodiments, the method for treating the sample in step (a) comprises contacting the sample with one or more compounds which are bound by hInL with high affinity selected from the group consisting of glycerol, 3-Keto-2-deoxyoctonic acid; D-glycerol-1-phosphate, D-mannoheptose, sepharose, sepharose-containing particles (i.e. latex, polystyrene or glass beads, microspheres or gels).

BRIEF DESCRIPTION OF THE DRAWINGS

The patent or application file contains at least one drawing executed in color. Copies of this patent or patent application publication with color drawings will be provided by the Office upon request and payment of the necessary fee.

Figure 3:
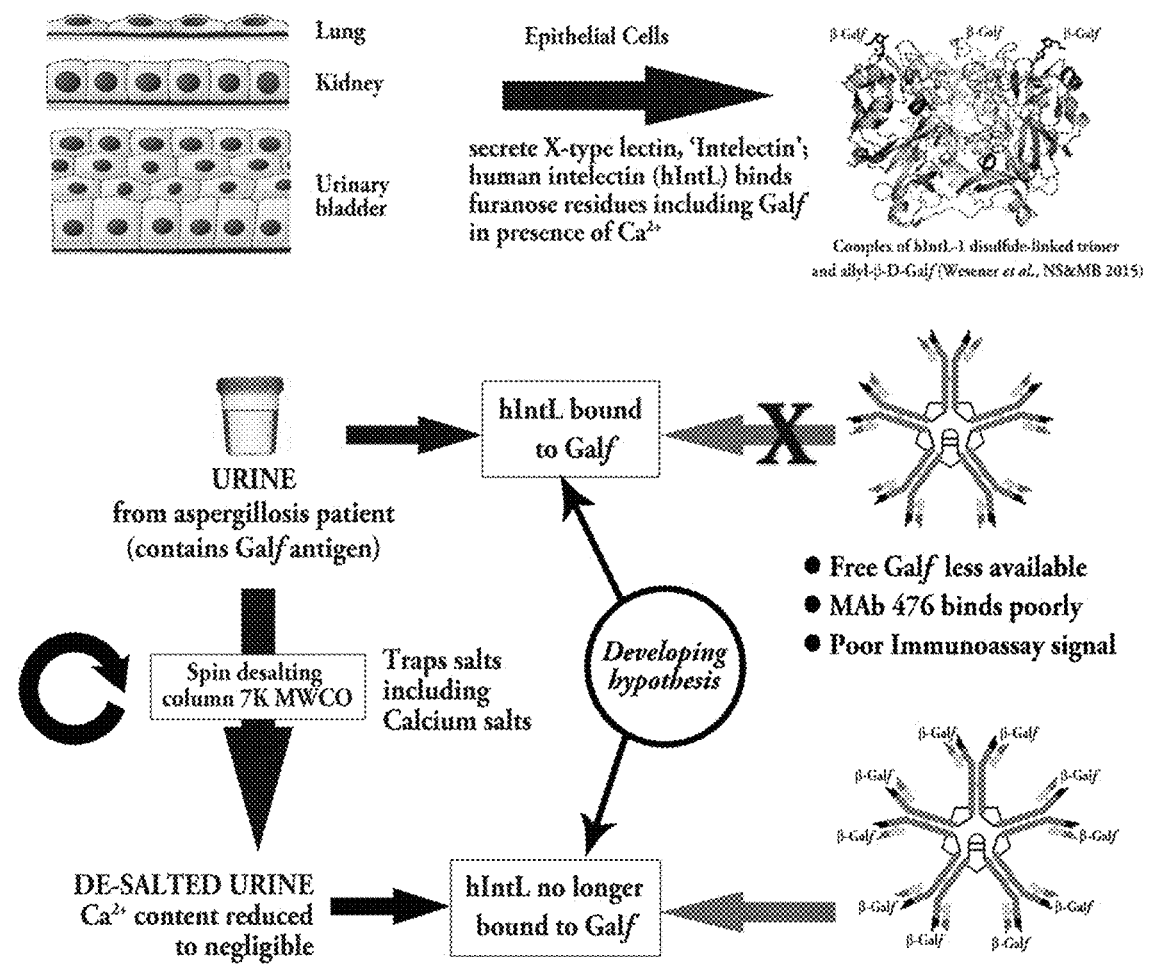

FIG. 3 shows the inventors' hypothesis that hIntL was secreted into the urine and was competitively binding to galF antigens in the presence of the inventors' monoclonal antibodies specific for galF, and that desalting removes $Ca^{2+}$ needed for hIntL to bind galF.

FIG. 9 shows localization of mAB476 antibody-reactive bands relative to the anti-hIntL antibody reactive bands.

DETAILED DESCRIPTION OF THE INVENTION

Figure 1:
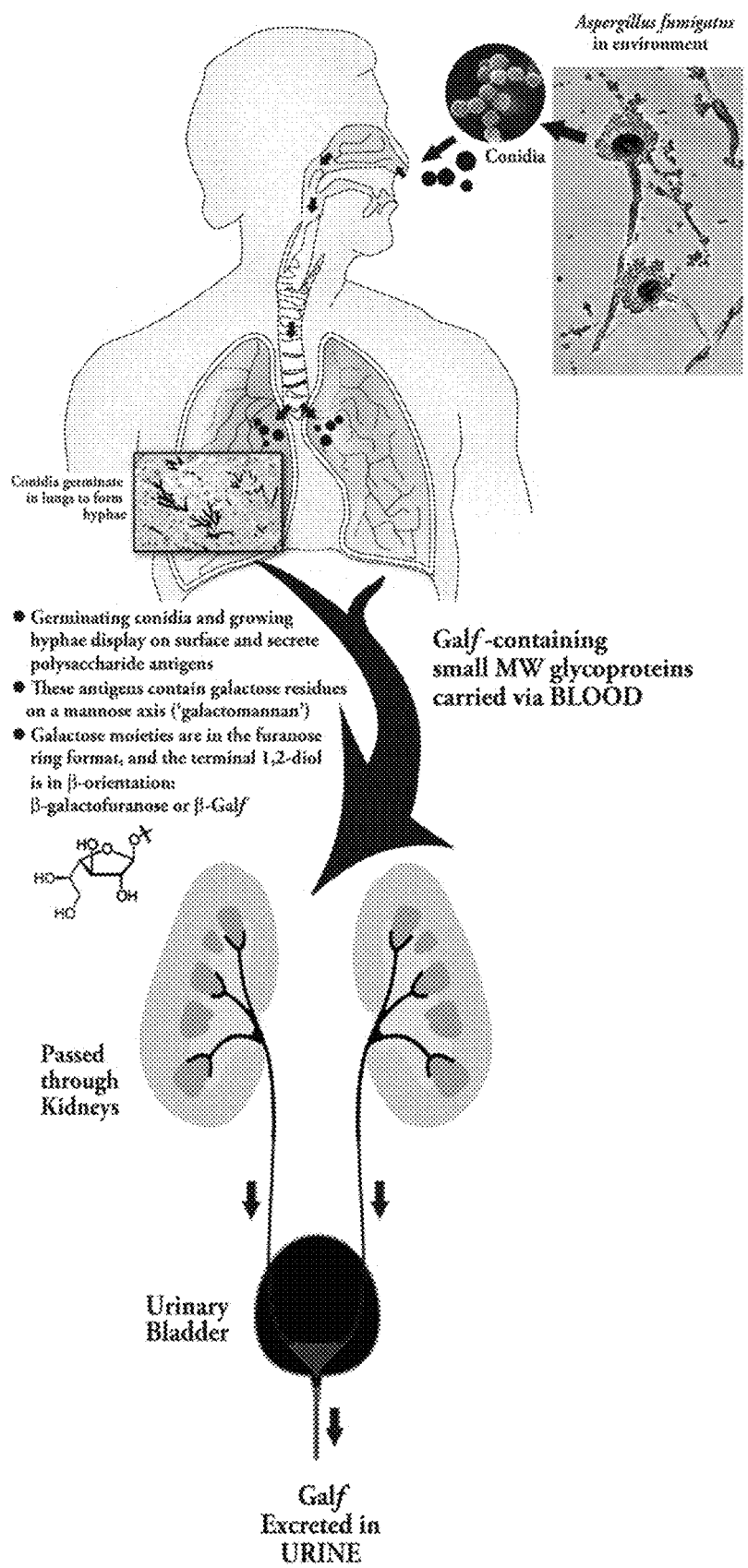
FIG. 1 illustrates the inventors' prior discovery of galF antigens in the urine of patients with *Aspergillus* infection and production of monoclonal antibodies specific for galF antigens, with sensitivity to detect excreted antigens in urine samples.
Figure 2:
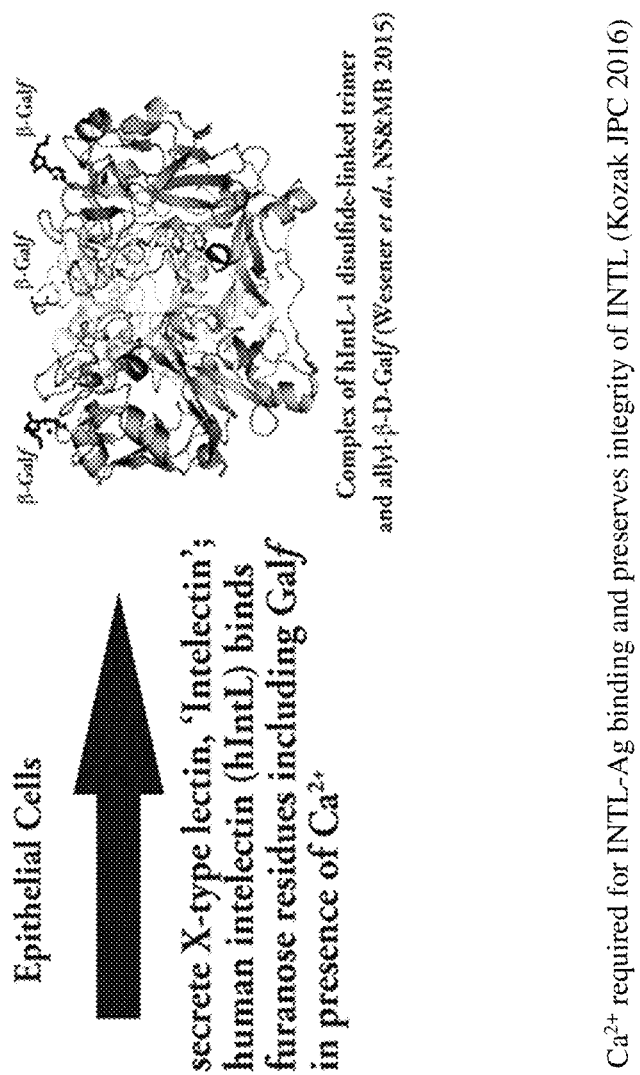
FIG. 2 shows intelectin and what is known about lectin molecules.

The following detailed description is exemplary and explanatory and is intended to provide further explanation of the present disclosure described herein. Other advantages, and novel features will be readily apparent to one of ordinary skill in the art from the following detailed description of the present disclosure.

Disclosed herein are methods of detecting microbial infection in mammalian subjects comprising treatment of a sample and detection of polysaccharide antigenic components utilizing monoclonal antibodies. The methods disclosed provide for pretreatment of biological samples, such as urine samples, to maximize detection of galF antigens and improvement of sensitivity of galF antigen detection assays.

The methods include minimizing hIntL binding to galF antigens and improvement of monoclonal antibody binding. The detection methods are useful for identifying the presence of microbial antigens related to *Streptococcus pneumoniae, Aspergillus* species, *Fusarium* species, *Coccidioides* species, *Cryptococcus* species, and *Histoplasma* species. In some embodiments, the microbial infection is caused by Prokaryotic and Eukaryotic pathogens that produce galF-containing antigens, including but not limited to, *Streptococcus* species, *Pseudomonas* species, *Nocardia* species, *Actinomyces* species. Zygomycetes and parasites, including but not limited to *Leishmania* species, and *Trypanosoma* species.

Intelectin was previously called 'omentin' as it is secreted from adipose cells and epithelial cells. Intelectin binds to molecules that contain sugar residues (such as galF), especially those produced by microbes and other non-mammalian organisms (ex. algae, plants). Intelectin is thought to be involved in host-defense as it is produced by epithelial cells facing the environment, such as those lining the airways and gut.

The antibody of the presently disclosed methods is, in some aspects, specific for at least one antigen containing a galactofuranose residue and is selected from the group consisting of monoclonal antibody 205 (MAb 205) comprising a variable heavy (VH) domain of SEQ ID NO:1 and a variable light (VL) domain of SEQ ID NO:2; monoclonal antibody 24 (MAb 24) comprising a VH domain of SEQ ID NO:3 and a VL domain of SEQ ID NO:4; monoclonal antibody 686 (MAb 686) comprising a VH domain of SEQ ID NO:5 and a VL domain of SEQ ID NO:6; monoclonal antibody 838 (MAb 838) comprising a VH domain of SEQ ID NO:7 and a VL domain of SEQ ID NO:8; and monoclonal antibody 476 (MAb 476) comprising a VH domain of SEQ ID NO:9 and a VL domain of SEQ ID NO:10. The presently disclosed methods are suitable for use in biological samples selected from the group consisting of urine, bronchoalveolar lavage (BAL) fluid, serum, gastrointestinal fluids, blood, saliva and cerebrospinal fluid (CSF).

In other embodiments, the presently disclosed subject matter provides a lateral flow device adapted to perform the presently disclosed methods for diagnosing a microbial infection in a biological sample of a mammalian subject suspected of having, having, or susceptible to having a microbial infection.

In accordance with some embodiments, presently disclosed subject matter provides a dipstick assay to perform the presently disclosed methods for diagnosing a microbial infection in a biological sample of a mammalian subject suspected of having, having, or susceptible to having a microbial infection.

In yet other embodiments, the presently disclosed subject matter provides an antibody specific for at least epitope of an antigen secreted by a microbial organism, wherein in particular aspects, the antigen comprises a galactofuranose residue.

Point-of-Care Diagnostics Such as Lateral Flow Devices and Dipstick Assays: Theory and Current Applications The ability to provide test results rapidly to the patient and/or healthcare provider is very important to impact outcomes of multiple conditions. Rapid tests to aid diagnosis and enable early detection of multiple diseases and physiologic conditions are being developed. Such tests are especially useful when they can be applied with self-testing and require little in the way of laboratory processing. Examples of point-of-care (POC) test devices in common use today include pregnancy and fertility tests, as well as assays to follow blood glucose in diabetics. Development of diagnostic tests for infections that use POC testing are especially important in resource-poor settings; for this reason, POC testing has become a new goal to be achieved for infections such as HIV, malaria, and hepatitis. Similarly, POC testing has the potential of impacting clinical outcomes when applied to infections that occur in the outpatient setting, not only by providing indications of disease, but by enabling development of more robust prevention algorithms.

Commonly used immunoassays in diagnostic and research use include radio-immunoassays and enzyme-linked immunosorbent assays (ELISAs). Many of these elaborately configured immunoassays use monoclonal antibodies (mAbs) that possess the ability to bind specifically to the analyte being tested, thereby enhancing the accuracy of the assay. Various approaches have been described for carrying out enzyme immunoassays. A considerable number of these approaches, starting with the earliest of ELISAs, are solid-phase immunoassays in which the analyte to be detected is bound to a solid matrix directly (Direct ELISA) or indirectly (Sandwich ELISA), in which the analyte is captured on a primary reagent. The choice of the solid matrix depends on procedural considerations. A common matrix is the polystyrene surface of multi-well microtiter plates.

These types of assays also are amenable to developing POC devices, in which systems can be self-contained so that output is readable by the user. This characteristic is especially useful when collection of a sample to be tested does not require medical intervention (e.g., urine, saliva, or sputum). One device that enables this is the lateral-flow device (LFD). These devices use a multi-layered construction containing both absorbent and non-absorbent components to form a solid-phase. The capture and/or recognition reagents (antigen or antibody) are pre-applied to specific areas within the assembled apparatus and the analyte is allowed to flow through the system to come into contact with reagents. Often, for the purpose of self-containment, the reagent components are added in a dried state so that fluid from the sample re-hydrates and activates them. Conventional ELISA techniques can then be used to detect the analyte in the antigen-antibody complex. In some embodiments, the system can be designed to provide a colorimetric reading for visual estimation of a binary response ('yes' or 'no'), or it can be configured to be quantitative.

Lateral flow devices are used to detect analytes in multiple body fluids, including serum and urine. To date, these types of devices have seen the most use for detecting circulating endogenous analytes; perhaps the most common use of this type of device is in the ubiquitous POC pregnancy test. Current efforts are being directed toward detecting microbial analytes, including nucleic acids, in the setting of viral infections (e.g., influenza, respiratory syncytial virus, and the like), Nielsen, K., et al., Prototype single step lateral flow technology for detection of avian influenza virus and chicken antibody to avian influenza virus. J Immunoassay Immunochem, 2007. 28(4): p. 307-18; Mokkapati, V. K., et al., Evaluation of UPlink-RSV: prototype rapid antigen test for detection of respiratory syncytial virus infection. Ann NY Acad Sci, 2007. 1098: p. 476-85; bacterial infections (e.g., *S. pneumoniae, Legionella, Mycobacteria*), Koide, M., et al., Comparative evaluation of Duopath *Legionella* lateral flow assay against the conventional culture method using *Legionella pneumophila* and *Legionella anisa* strains. Jpn J Infect Dis, 2007. 60(4): p. 214-6.

One assay that is in use worldwide is the BinaxNOW pneumococcal urinary antigen test; this assay evolved after the serum-based platform was shown to be effective, but cumbersome. The urinary POC device can be particularly useful when employed in high-risk patients as a POC testing device. Roson, B., et al., Contribution of a urinary antigen assay (Binax NOW) to the early diagnosis of pneumococcal pneumonia. Clin Infect Dis, 2004. 38(2): p. 222-6; Weatherall, C., R. Paoloni, and T. Gottlieb, Point-of-care urinary pneumococcal antigen test in the emergency department for community acquired pneumonia. Emerg Med J, 2008. 25(3): p. 144-8. This issue is particularly relevant in the context of the presently disclosed subject matter, as the polysaccharides in the pneumococcus capsule have some structural similarity to those of *Aspergillus*. Kappe, R. and A. Schulze-Berge, New cause for false-positive results with the Pastorex *Aspergillus* antigen latex agglutination test. J Clin Microbiol, 1993. 31(9): p. 2489-90; Stynen, D., et al., Rat monoclonal antibodies against *Aspergillus galactomannan*. Infect Immun, 1992. 60(6): p. 2237-45; Swanink, C. M., et al., Specificity of a sandwich enzyme-linked immunosorbent assay for detecting *Aspergillus galactomannan*. J Clin Microbiol, 1997. 35(1): p. 257-60.

Lateral Flow Device and Optimized Methods of Use Thereof for Diagnosing Microbial Infections Preliminary studies have demonstrated that antigens of *A. fumigatus* (e.g., galF) are renally concentrated in animal model and are excreted in urine such that the sensitivity and specificity of a urine-based assay may equal or exceed that of serum based testing. Urinary detection of antigens would enable development of an easy-to-use POC testing method that would enable frequent testing in the outpatient setting, thus aiding the ability to diagnose and optimize screening strategies employed to detect infection early in the course of disease. Accordingly, in some embodiments, the presently disclosed subject matter provides a POC test to detect *Aspergillus* galF-containing antigens in urine. Monoclonal antibodies that recognize galactofuranose residues of *A. fumigatus* galF have been developed and are used in the presently disclosed galF test.

A standard ELISA format was used as a screen to identify antibodies to use for capture on the immobilized device. The identified antibody can be used as a capture antibody with point of care testing device (strip), which can be optimized for conditions to detect galF-antigen (antibody concentration, incubation conditions, and the like).

The term "dipstick assay" as used herein means any assay using a dipstick in which sample solution is contacted with the dipstick to cause sample solution to move by capillary action to a capture zone of the dipstick thereby allowing a target antigen in the sample solution to be captured and detected at the capture zone. To test for the presence of analyte, the contact end of the dipstick is contacted with the test solution. If analyte is present in the test solution it travels to the capture zone of the dipstick by capillary action where it is captured by the capture antibody. The presence of analyte at the capture zone of the dipstick is detected by a further anti-analyte antibody (the detection antibody) labelled with, for example, colloidal gold.

These dipstick tests have several advantages. They are easy and cheap to perform, no specialist instruments are required, and the results are obtained rapidly and can be read visually. These tests are, therefore, particularly suited for use in a physician's office, at home, in remote areas, and in developing countries where specialist equipment may not be available. They can be used, for example, to test whether a patient is infected with a disease causing microorganism such as *A. fumigatus*.

To perform a method of the first aspect of the invention, the targeting agent and labels may simply be added to the test solution and the test solution then contacted with the contact end of the chromatographic strip. Such methods are easier to perform than the method disclosed in WO 00/25135 in which two separate wicking steps are required. The results may, therefore, be obtained more rapidly, and yet the sensitivity of analyte detection is higher.

The term "chromatographic strip" is used herein to mean any porous strip of material capable of transporting a solution by capillarity. The chromatographic strip may be capable of bibulous or non-bibulous lateral flow, but preferably bibulous lateral flow. By the term "non-bibulous lateral flow" is meant liquid flow in which all of the dissolved or dispersed components of the liquid are carried at substantially equal rates and with relatively unimpaired flow laterally through the membrane as opposed to preferential retention of one or more components as would occur with "bibulous lateral flow." Materials capable of bibulous lateral flow include paper, nitrocellulose, and nylon. A preferred example is nitrocellulose.

The labels may be bound to the ligands of the targeting agent by pre-mixing the targeting agent with the labels before the targeting agent is added to (or otherwise contacted with) the test solution. However, in some circumstances, it is preferred that the targeting agent and labels are not pre-mixed because such pre-mixing can cause the targeting agent and labels to precipitate. Thus, the targeting agent and the labels may be added separately to (or contacted separately with) the test solution. The targeting agent and the labels can be added to (or contacted with) the test solution at substantially the same time, or in any order.

The test solution may be pre-incubated with the targeting agent and labels before the test solution is contacted with the contact end of the chromatographic strip to ensure complex formation. The optimal time of pre-incubation will depend on the ratio of the reagents and the flow rate of the chromatographic strip. In some cases, pre-incubation for too long can decrease the detection signal obtained, and even lead to false positive detection signals. Thus, it may be necessary to optimize the pre-incubation time for the particular conditions used.

It may be desired to pre-incubate the targeting agent with the test solution before binding the labels to the targeting agent so that the targeting agent can be allowed to bind to analyte in the test solution under optimum binding conditions. Generally, the presently disclosed subject matter provides a method for diagnosing a microbial infection in a biological sample from a mammalian subject suspected of having, having, or susceptible to having a microbial infection, by detecting the presence of at least one antigen comprising a galF residue in a biological sample of the mammalian subject, the method comprising: (a) treating the biological sample to decrease or minimize human IntL-1 binding of galF residues present in the sample; (b) contacting the treated sample of (a) with at least one antibody specific for at least one antigen comprising a galF residue in an effective amount to produce a detectable amount of antibody-galF antigen complex; and (c) detecting the presence of at least one antibody-galF antigen complex, wherein the detection of the presence of at least one antibody-galF antigen complex is diagnostic of a microbial infection in a mammalian subject.

In accordance with another embodiment, the present invention provides a method for diagnosing a microbial infection in a biological sample from a mammalian subject suspected of having, having, or susceptible to having a microbial infection by detecting the presence of at least one antigen comprising a galF residue in a biological sample of the mammalian subject, the method comprising: (a) treating the biological sample comprising contacting the sample with a substrate such as a ligand which binds directly to intelectin, or calcium or mono and divalent cations with high affinity, to inhibit hIntL binding of galF residues present in the sample; (b) contacting the treated sample of (a) with at least one antibody specific for at least one antigen comprising a galF residue in an effective amount to produce a detectable amount of antibody-galF antigen complex; and (c) detecting the presence of at least one antibody-galF antigen complex, wherein the detection of the presence of at least one antibody-galF antigen complex is diagnostic of a microbial infection in a mammalian subject.

The microbial infection can be selected from the group consisting of a bacterial infection and a fungal infection. In some embodiments, the bacterial infection is caused by an infection of *Streptococcus pneumoniae*. In other embodiments the microbial infection is a fungal infection caused by an infection of an organism selected from the group consisting of *Aspergillus* species, *Fusarium* species, *Coccidiodes* species, *Cryptococcus* species, and *Histoplasma* species.

In some embodiments, the microbial infection is caused by Prokaryotic and Eukaryotic pathogens that produce galF-containing antigens, including but not limited to, *Streptococcus* species, *Pseudomonas* species, *Nocardia* species, *Actinomyces* species. Zygomycetes and parasites, including but not limited to *Leishmania* species, and *Trypanosoma* species.

In particular embodiments, at least one antibody specific for at least one antigen comprising a galactofuranose residue is selected from the group consisting of monoclonal antibody 205 (MAb 205) comprising a variable heavy (VH) domain of SEQ ID NO:1 and a variable light (VL) domain of SEQ ID NO:2; monoclonal antibody 24 (MAb 24) comprising a VH domain of SEQ ID NO:3 and a VL domain of SEQ ID NO:4; monoclonal antibody 686 (MAb 686) comprising a VH domain of SEQ ID NO:5 and a VL domain of SEQ ID NO:6; monoclonal antibody 838 (MAb 838) comprising a VH domain of SEQ ID NO:7 and a VL domain of SEQ ID NO:8; and monoclonal antibody 476 (MAb 476) comprising a VH domain of SEQ ID NO:9 and a VL domain of SEQ ID NO:10.

One of ordinary skill in the art upon review of the presently disclosed subject matter would appreciate that any biological fluid in which at least one antigen comprising a galactofuranose residue is secreted is suitable for use with the presently disclosed methods. In particular embodiments, the biological sample is selected from the group consisting of urine, bronchoalveolar lavage (BAL) fluid, serum, gastrointestinal fluids, blood, and cerebrospinal fluid (CSF).

In some embodiments, the presently disclosed methods further comprise pre-treating the biological sample before contacting the biological sample with at least one antibody specific for at least one antigen comprising a galactofuranose residue. The pre-treating step can include a step selected from the group consisting of filtering, diluting, and concentrating the biological sample, and combinations thereof.

Without being held to any particular theory, the Mab476 antibody used in the methods of the present invention is thought to bind to the galF-containing O-glycan moiety/moieties associated with cellulose (CelA) protein. As described above, the Mab476 antibody may bind to galF from any origin, including galF that is present on extracellular vesicles shed by the infectious organism.

In accordance with some embodiments, the method for treating the sample in step (a) comprises contacting the sample with a substrate which binds $Ca^{2+}$ ions with high affinity.

Examples of substrates which can bind divalent cations with high affinity include, for example, N,N,N',N'-tetrakis-(2-pyridylmethyl)ethylenediamine (TPEN, membrane-permeable chelator) and diethylenetriaminepentaacetic acid (DTPA, membrane-impermeable chelator), and cation exchange resins such as AG50, Chelex, poly(acrylic acid).

In accordance with some embodiments, the method for treating the sample in step (a) comprises contacting the sample with a compound which chelates $Ca^{2+}$ ions with high affinity. Examples of chelators include, without limitation, ethylenediamine tetraacetic acid (EDTA), Ethylene glycol-bis(2-aminoethylether)-N,N,N',N'-tetraacetic acid (EGTA), 1,2-bis(o-Aminophenoxy)ethane-N,N,N',N'-tetraacetic Acid (BAPTA), 1-(2-Nitro-4,5-dimethoxyphenyl)-1,2-diaminoethane-N,N,N',N'-tetraacetic Acid, 4Na, Dimethoxynitrophenamine (DM-Nitrophen), and others.

In accordance with some embodiments, the method for treating the sample in step (a) comprises contacting the sample with EDTA and/or EGTA.

In accordance with some embodiments, the method for treating the sample in step (a) comprises contacting the sample with a substrate which binds hIntL-1 with high affinity.

Examples of compounds which bind hIntL-1 include, but are not limited to, glycerol, 3-keto-2-deoxyoctonic acid, D-glycerol-1-phosphate, D-mannoheptose, and other compounds which are bound by hIntL-1.

In accordance with some embodiments, the method for treating the sample in step (a) comprises contacting the sample with an antibody specific for hIntL-1. In some embodiments, the antibody can be rabbit polyclonal IgG anti-hIntL-1 antibody.

In accordance with some embodiments, the method for treating the sample in step (a) comprises contacting the sample with one or more compounds which are bound by hIntL-1 with high affinity.

In accordance with some embodiments, the method for treating the sample in step (a) comprises contacting the sample with one or more compounds which bind hIntL with high affinity selected from the group consisting of glycerol, 3-Keto-2-deoxyoctonic acid; D-glycerol-1-phosphate, D-mannoheptose, sepharose, sepharose-containing particles (i.e. latex, polystyrene or glass beads, microspheres or gels).

In accordance with some embodiments, the method for treating the sample in step (a) comprises a combination of one or more of the above methods including, for example, treating the sample with a chelator and one or more compounds which are bound by hIntL with high affinity, and an anti-IntL antibody. Any of the above methods can be combined to further prevent hIntL-1 from binding galF in a biological sample.

In accordance with some embodiments, the method for treating the sample in step (a) comprises contacting the sample with a desalting column. Examples of desalting columns are known in the art, including, for example, desalting columns which are pre-packed with polyacrylamide size exclusion resins.

The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein. In particular embodiments, the subject is a human adult suspected of having, having, or susceptible of having a microbial infection. In other embodiments, the subject is a human child, e.g., a human less than about 19 years of age, suspected of having, having, or susceptible of having a microbial infection.

The presently disclosed methods can be used to diagnose, for the prognosis, or the monitoring of a disease state or condition. As used herein, the term "diagnosis" refers to a predictive process in which the presence, absence, severity or course of treatment of a disease, disorder or other medical condition is assessed. For purposes herein, diagnosis also includes predictive processes for determining the outcome resulting from a treatment. Likewise, the term "diagnosing," refers to the determination of whether a sample specimen exhibits one or more characteristics of a condition or disease. The term "diagnosing" includes establishing the presence or absence of, for example, a target antigen or reagent bound targets, or establishing, or otherwise determining one or more characteristics of a condition or disease, including type, grade, stage, or similar conditions. As used herein, the term "diagnosing" can include distinguishing one form of a disease from another. The term "diagnosing" encompasses the initial diagnosis or detection, prognosis, and monitoring of a condition or disease.

The term "prognosis," and derivations thereof, refers to the determination or prediction of the course of a disease or condition. The course of a disease or condition can be determined, for example, based on life expectancy or quality of life. "Prognosis" includes the determination of the time course of a disease or condition, with or without a treatment or treatments. In the instance where treatment(s) are contemplated, the prognosis includes determining the efficacy of a treatment for a disease or condition.

As used herein, the term "risk" refers to a predictive process in which the probability of a particular outcome is assessed. The term "monitoring," such as in "monitoring the course of a disease or condition," refers to the ongoing diagnosis of samples obtained from a subject having or suspected of having a disease or condition. The term "marker" refers to a molecule, including an antigen, such as a polysaccharide, that when detected in a sample is characteristic of or indicates the presence of a disease or condition.

Accordingly, in some embodiments, the presently disclosed subject matter provides a method for diagnosing of a microbial infection in a mammalian subject suspected of having, having, or susceptible to having a microbial infection, wherein the method comprises monitoring a treatment regimen of a microbial infection to determine the efficacy of the treatment regimen.

In accordance with some embodiments, the methods disclosed herein can be used with lateral flow devices such as those disclosed in in U.S. patent application Ser. No. 13/511,264, and incorporated by reference herein in its entirety. The presently disclosed methods can use a lateral flow device or dipstick assay comprising an immunochromatographic strip test that relies on a direct (double antibody sandwich) reaction. Without wishing to be bound to any one particular theory, this direct reaction scheme is best used when sampling for larger analytes that may have multiple antigenic sites. Different antibody combinations can be used, for example different antibodies can be included on the capture (detection) line, the control line, and included in the mobile phase of the assay, for example, as conjugated to gold particles, e.g., gold microparticles or gold nanoparticles.

In an embodiment, the present disclosure comprises kits for diagnosing a microbial infection in a biological sample from a mammalian subject suspected of having, having, or susceptible to having a microbial infection by detecting the presence of at least one antigen comprising a galactofuranose residue in a biological sample of the mammalian subject. Such kits may include all necessary reagents, components, apparatus and instructions for treating the biological sample to inhibit human intelectin (hIntL) binding of galactofuranose residues present in the sample; in an embodiment, the kits may further comprise at least one antibody specific for at least one antigen comprising a galactofuranose residue in an effective amount to produce a detectable amount of antibody-galF antigen complex; in an embodiment, the kit further enables detecting the presence of at least one antibody-galF antigen complex, wherein the detection of the presence of at least one antibody-galF antigen complex is diagnostic of a microbial infection in a mammalian subject. In certain embodiments, the kit comprises the use of a lateral flow apparatus, dipstick, assay stick with immunochromatographic detection display, and any such apparatus know to those skilled in the art. In certain embodiments, reagents and/or detection components may be immobilized on the apparatus itself (i.e. on the dipstick). In certain embodiments, reagents for chelating calcium are included in the kit.

As used herein the term "lateral flow" refers to liquid flow along the plane of a substrate or carrier, e.g., a lateral flow membrane. In general, lateral flow devices comprise a strip (or a plurality of strips in fluid communication) of material capable of transporting a solution by capillary action, i.e., a wicking or chromatographic action, wherein different areas or zones in the strip(s) contain assay reagents, which are either diffusively or non-diffusively bound to the substrate, that produce a detectable signal as the solution is transported to or migrates through such zones. Typically, such assays comprise an application zone adapted to receive a liquid sample, a reagent zone spaced laterally from and in fluid communication with the application zone, and a detection zone spaced laterally from and in fluid communication with the reagent zone. The reagent zone can comprise a compound that is mobile in the liquid and capable of interacting with an analyte in the sample, e.g., to form an analyte-reagent complex, and/or with a molecule bound in the detection zone. The detection zone may comprise a binding molecule that is immobilized on the strip and is capable of interacting with the analyte and/or the reagent and/or an analyte-reagent complex to produce a detectable signal.

Such assays can be used to detect an analyte in a sample through direct (sandwich assay) or competitive binding. Examples of lateral flow devices are provided in U.S. Pat. No. 6,194,220 to Malick et al.; U.S. Pat. No. 5,998,221 to Malick et al.; U.S. Pat. No. 5,798,273 to Shuler et al.; and RE38,430 to Rosenstein.

In some embodiments, the presently disclosed methods can be used with an assay comprising a sandwich lateral flow or dipstick assay. In a sandwich assay, a liquid sample that may or may not contain an analyte of interest is applied to the application zone and allowed to pass into the reagent zone by capillary action. The term "analyte" as used herein refers to an antigen comprising a galactofuranose residue. In certain embodiments the presence or absence of an analyte in a sample is determined qualitatively. In other embodiments, a quantitative determination of the amount or concentration of analyte in the sample is determined.

The analyte, if present, interacts with a labeled reagent in the reagent zone to form an analyte-reagent complex and the analyte-reagent complex moves by capillary action to the detection zone. The analyte-reagent complex becomes trapped in the detection zone by interacting with a binding molecule specific for the analyte and/or reagent. Unbound sample can pass through the detection zone by capillary action to a control zone or an absorbent pad laterally juxtaposed and in fluid communication with the detection zone. The labeled reagent may then be detected in the detection zone by appropriate means.

Generally, and without limitation, lateral flow devices comprise a sample pad. A sample pad comprises a membrane surface, also referred to herein as a "sample application zone," adapted to receive a liquid sample. A standard cellulose sample pad has been shown to facilitate absorption and flow of biological samples, including, but not limited to, urine. The sample pad comprises a portion of lateral flow device that is in direct contact with the liquid sample, that is, it receives the sample to be tested for the analyte of interest. The sample pad can be part of, or separate from, a lateral flow membrane. Accordingly, the liquid sample can migrate, through lateral or capillary flow, from sample pad toward a portion of the lateral flow membrane comprising a detection zone. The sample pad is in fluid communication with the lateral flow membrane comprising an analyte detection zone. This fluid communication can arise through either be an overlap, top-to-bottom, or an end-to-end fluid connection between the sample pad and a lateral flow membrane. In certain embodiments, the sample pad comprises a porous material, for example and not limited to, paper. In certain embodiments the targeting agent, molecule or other reagent of the diagnostic method may be immobilized on the conjugate pad. In certain embodiments, the targeting agent, molecule or other reagent of the diagnostic method may be present in an alternative format.

The term "sample" as used herein refers to any biological sample suspected of containing an analyte for detection or a control sample expected to be substantially free of the analyte of interest. In particular embodiments, the sample comprises a biological fluid of a subject suspected of having, having, or susceptible of having a microbial infection. In some embodiments, the biological sample is in liquid form, while in other embodiments it can be changed into a liquid form, e.g., by reconstitution in a suitable solvent, e.g., an aqueous solution. The presently disclosed lateral flow devices are suitable for use with a variety of biological samples including, but not limited to, urine, bronchoalveolar lavage (BAL) fluid, serum, blood, gastrointestinal fluids, and cerebrospinal fluid (CSF).

Typically, a sample pad is positioned adjacent to and in fluid communication with a conjugate pad. A conjugate pad comprises a labeled reagent having specificity for one or more analytes of interest. In some embodiments, the conjugate pad comprises a non-absorbent, synthetic material (e.g., polyester) to ensure release of its contents. A detection conjugate is dried into place on the conjugate pad and only released when the liquid sample is applied to the sample pad. Detection conjugate can be added to the pad by immersion or spraying.

In particular embodiments, the detection conjugate comprises an antibody having specificity for a antigen comprising a galactofuranose residue. In representative embodiments, the antibody is selected from the group consisting of monoclonal antibody 205 (MAb 205) comprising a variable heavy (VH) domain of SEQ ID NO:1 and a variable light (VL) domain of SEQ ID NO:2; monoclonal antibody 24 (MAb 24) comprising a VH domain of SEQ ID NO:3 and a VL domain of SEQ ID NO:4; monoclonal antibody 686 (MAb 686) comprising a VH domain of SEQ ID NO:5 and a VL domain of SEQ ID NO:6; monoclonal antibody 838 (MAb 838) comprising a VH domain of SEQ ID NO:7 and a VL domain of SEQ ID NO:8; and monoclonal antibody 476 (MAb 476) comprising a VH domain of SEQ ID NO:9 and a VL domain of SEQ ID NO:10. The antibody, e.g., a monoclonal antibody (MAb), can be conjugated to a gold particle, e.g., colloidal gold, including gold microspheres, or gold nanoparticles. For example, it is possible to biotinylate the conjugated MAb to take advantage of the strong affinity that biotin has for streptavidin, using Streptavidin-coated microspheres. Alternatives include protein A-coated microspheres that bind to Fc region of IgGs. Conditions to define optimal optimization to colloidal gold can be determined, for example, in microtiter wells. For example, 100 µL of colloidal gold at 1 OD530 can be added to each well, followed by 10 µL of 22 mM buffers (MES, HEPES) at variable pH (5.5 to 10, in 0.5 increments). Antibodies can be added at concentrations ranging from about 1.25 µg/l OD colloid to about 10 µg/l OD colloid, incubated for 15 minutes, and then 25 µL of 1.5 NaCl can be added. Conjugated particles will be stable and pink; the optimal condition that requires the lowest concentration of antibodies can be determined.

It is contemplated that any detection agent used in the present disclosure will be labeled with any "reporter molecule," so that it is detectable in any detection system, including, but not limited to enzyme (e.g., ELISA, as well as enzyme-based histochemical assays), fluorescent, radioactive, and luminescent systems. It is not intended that the present invention be limited to any particular detection system or label. Furthermore, it is contemplated that screening for the target will be accomplished by techniques known in the art (e.g., radioimmunoassay, ELISA (enzyme-linked immunosorbant assay), "sandwich" immunoassays, immunoradiometric assays, gel diffusion precipitation reactions, immuNIPA-liffusion assays, in situ immunoassays (e.g., using colloidal gold, enzyme or radioisotope labels), Western blots, precipitation reactions, agglutination assays (e.g., gel agglutination assays, hemagglutination assays, etc.), complement fixation assays, immunofluorescence assays, color emitting nanoparticles (e.g. quantum dots), protein A assays, and immunoelectrophoresis assays, etc. Such methodologies and techniques are known to those skilled in the art.

Usually, the conjugate pad is adjacent to and in fluid communication with a lateral flow membrane. Capillary action draws a fluid mixture up the sample pad, through the conjugate pad where an antibody-galF antigen complex is formed, and into the lateral flow membrane. Lateral flow is a function of the properties of the lateral flow membrane. The lateral flow membrane typically is extremely thin and is hydrophilic enough to be wetted, thereby permitting unimpeded lateral flow and mixture of reactants and analytes at essentially the same rates.

Lateral flow membranes can comprise any substrate capable of providing liquid flow including, but not limited to, substrates, such as nitrocellulose, nitrocellulose blends with polyester or cellulose, untreated paper, porous paper, rayon, glass fiber, acrylonitrile copolymer, plastic, glass, or nylon. Lateral flow membranes can be porous. Typically, the pores of a lateral flow membrane are of sufficient size such that particles, e.g., microparticles comprising a reagent capable of forming a complex with an analyte, flow through the entirety of the membrane. Lateral flow membranes, in general, can have a pore size ranging from about 3 µm to about 100 µm, and, in some embodiments, have a pore size ranging from about 10 µm to about 50 µm. Pore size affects capillary flow rate and the overall performance of the device.

There are multiple benefits to using nitrocellulose for the primary membrane: low cost, capillary flow, high affinity for protein biding, and ease of handling. Nitrocellulose has high protein binding. Another alternative is cellulose acetate, which has low protein binding. Size dictating surface area dictates membrane capacity (the volume of sample that can pass through the membrane per unit time=length×width×thickness×porosity. Because these variables control the rate at which lateral flow occurs, they can impact sensitivity and specificity of the assay. The flow rate also varies with sample viscosity. Several different sizes and polymers are available for use as microspheres, which migrate down the membrane with introduction of the fluidic sample. The optimal flow rate generally is achieved using spheres that are 1/10 the pore size of the membrane or smaller.

One skilled in the art will be aware of other materials that allow liquid flow. Lateral flow membranes, in some embodiments, can comprise one or more substrates in fluid communication. For example, a conjugate pad can be present on the same substrate or may be present on separate substrates (i.e., pads) within or in fluid communication with lateral flow membranes. In some embodiments, the nitrocellulose membrane can comprise a very thin Mylar sheet coated with a nitrocellulose layer.

Lateral flow membranes can further comprise at least one indicator zone or detection zone. The terms "indicator zone" and "detection zone" are used interchangeably herein and mean the portion of the carrier or porous membrane comprising an immobilized binding reagent. As used herein, the term "binding reagent" means any molecule or a molecule bound to a particle, wherein the molecule recognizes or binds the analyte in question. The binding reagent is capable of forming a binding complex with the analyte-labeled reagent complex. The binding reagent is immobilized in the detection zone and is not affected by the lateral flow of the liquid sample due to the immobilization on the membrane. Once the binding reagent binds the analyte-labeled reagent complex it prevents the analyte-labeled reagent complex from continuing with the flow of the liquid sample. In some embodiments, the binding reagent is an antibody having specificity for an antigen having at least one galactofuranose residue.

Accordingly, during the actual reaction between the analyte and the reagent, the first member binds in the indicator zone to the second member and the resulting bound complex is detected with specific antibodies. Detection may use any of a variety of labels and/or markers, e.g., enzymes (alkaline phosphatase or horseradish peroxidase with appropriate substrates), radioisotopes, liposomes or latex beads impregnated with fluorescent tags, polymer dyes or colored nanoparticles, and the like. Thus, the result can be interpreted by any direct or indirect reaction. Colloidal gold particles, which impart a purple or red coloration, are most commonly used currently.

The capture and immobilization of the assay reagent (complementary member of the binding pair) at the indicator zone can be accomplished by covalent bonding or, more commonly, by adsorption, such as by drying. Such capture also can be indirect, for example, by binding of latex beads coated with the reagent. Depending on the nature of the material comprising the lateral flow membrane, covalent bonding may be enabled, for example with use of glutaraldehyde or a carbodiimide. In immunoassays, most common binding pairs are antigen-antibody pairs; however, multiple other binding pairs can be performed, such as enzyme-substrate and receptor-ligand.

In some embodiments, the indicator zone further comprises a test line and a control line. A test line can comprise an immobilized binding reagent. When antibodies are used to develop a test line in the LFD that employs a sandwich type of assay, they are applied at a ratio of about 1-3 µg/cm across the width of a strip 1 mm wide; hence, antibody concentration is about 10-30 µg/cm$^2$, which is about 25-100 fold that used in an ELISA. Brown, M. C., *Antibodies: key to a robust lateral flow immunoassay*, in *Lateral Flow Immunoassay*, H. Y. T. R. C. Wong, Editor. 2009, Humana Press: New York, N.Y. p. 59-74.

Further, in some embodiments, the presently disclosed lateral flow assays can be used to detect multiple analytes in a sample. For example, in a lateral flow assay, the reagent zone can comprise multiple labeled reagents, each capable of binding to a different analyte in a liquid sample or a single labeled reagent capable of binding to multiple analytes. If multiple labeled reagents are used in a lateral flow assay, the reagents may be differentially labeled to distinguish different types of analytes in a liquid sample.

It also is possible to place multiple lines of capture antibodies on the membrane to detect different analytes. Combinations of antibodies that detect different epitopes of glycans may optimize specificity if it is found that one antibody performs at a low quantitative limit of detection, yet exhibits some degree of nonspecific binding (or binding to urine components in control animals). One possibility is that the device may be adapted to detect galF and another fungal component to increase the potential spectrum of pathogens detected and to increase specificity of the reaction. *Aspergillus* species are thought to secrete galF and other fungal components, while glycans from other 'contaminants' should not contain other fungal components.

For quality control, typically a lateral flow membrane can include a control zone comprising a control line. The term "control zone" refers to a portion of the test device comprising a binding molecule configured to capture the labeled reagent. In a lateral flow assay, the control zone may be in liquid flow contact with the detection zone of the carrier, such that the labeled reagent is captured on the control line as the liquid sample is transported out of the detection zone by capillary action. Detection of the labeled reagent on the control line confirms that the assay is functioning for its intended purpose. Placement of a control line can be accomplished using a microprocessor controlled TLC spotter, in which a dispenser pump releases a constant volume of reagent across the membrane.

A typical lateral flow device can also comprises an absorbent pad. The absorbent pad comprises an "absorbent material," which as used herein, refers to a porous material having an absorbing capacity sufficient to absorb substantially all the liquids of the assay reagents and any wash solutions and, optionally, to initiate capillary action and draw the assay liquids through the test device. Suitable absorbent materials include, for example, nitrocellulose, nitrocellulose blends with polyester or cellulose, untreated paper, porous paper, rayon, glass fiber, acrylonitrile copolymer, plastic, glass, or nylon.

In some embodiments, a lateral flow membrane is bound to one or more substantially fluid-impervious sheets, one on either side, e.g., a bottom sheet and a complimentary top sheet with one or more windows defining an application zone and an indicator zone.

A typical lateral flow device also can include a housing. The term "housing" refers to any suitable enclosure for the presently disclosed lateral flow devices. Exemplary housings will be known to those skilled in the art. The housing can have, for example, a base portion and a lid portion. The lid portion can include a top wall and a substantially vertical side wall. A rim may project upwardly from the top wall and may further define a recess adapted to collect a sample from a subject. Suitable housings include those provided in U.S. Pat. No. 7,052,831 to Fletcher et al and those used in the BD Directigen™ EZ RSV lateral flow assay device.

As with the general method described immediately hereinabove, the microbial infection can be selected from the group consisting of a bacterial infection and a fungal infection. In some embodiments, the bacterial infection is caused by an infection of *Streptococcus pneumoniae*. In particular embodiments, the microbial infection is a fungal infection caused by an infection of an organism selected from the group consisting *Aspergillus* species, *Fusarium* species, *Coccidioides* species, *Cryptococcus* species, *Histoplasma* species and Zygomycetes.

In some embodiments, the microbial infection is caused by an organism having a propensity to cause lung infection, including but not limited to, *Streptococcus* species, *Pseudomonas* species, *Nocardia* species, *Actinomyces* species, Mycobacteria species as well as fungal organisms such as *Aspergillus* species, *Cryptococcus* species, *Histoplasma* species, and Zygomycetes.

In some embodiments, an antigen having a galactofuranose residue can be measured in whole, unconcentrated, or otherwise unprocessed, biological samples using the presently disclosed methods and devices. In other embodiments, the biological sample can be processed, e.g., concentrated, diluted, filtered, and the like, prior to performing the test. The pre-treatment of the urine sample can include diluting the urine sample in an aqueous solution, concentrating the urine sample, filtering the urine sample, or a combination thereof.

One of ordinary skill in the art upon review of the presently disclosed subject matter would appreciate that the pre-treatment steps can be performed in any particular order, e.g., in some embodiments, the sample can be diluted or concentrated and then filtered, whereas in other embodiments, the sample can be filtered and then diluted or concentrated. In particular embodiments, the presently disclosed methods include filtering the urine sample, for example, through a desalting column, to remove an inhibitor that interferes with the detection of antigen in the urine sample. This step can be performed with or without any further dilution or concentration of the sample.

Thus, in some embodiments, the lateral flow device further comprises an apparatus adapted to pre-treat the biological sample before contacting the biological sample with at least one antibody specific for at least one polysaccharide comprising a galF residue. In particular embodiments, the apparatus is adapted to filter, dilute, or concentrate the biological sample, or combinations thereof. More particularly, the apparatus can be adapted to remove an inhibitor that interferes with the detection of the at least one antigen comprising a galF residue in the biological sample, in particular, a urine sample.

In other embodiments, different parameters of the test, e.g., incubation time, can be manipulated to increase sensitivity and/or specificity of the test to eliminate the need for processing the biological sample. Accordingly, in some embodiments, the presently disclosed subject matter provides an antibody specific for at least epitope of an antigen secreted by a microbial organism. In particular embodiments, the antigen comprises a galF residue. In more particular embodiments, the antibody is specific for at least one epitope of an antigen secreted by a microbial organism selected from the group consisting of *Aspergillus* species, *Fusarium* species, *Coccidioides* species, *Cryptococcus* species, *Histoplasma* species, Zygomycetes and certain *Streptococcus* species. In additional embodiments, the antibody is specific for at least one epitope of a polysaccharide secreted by a microbial organism selected from the group consisting of *Streptococcus* species, *Pseudomonas* species, *Nocardia* species, *Actinomyces* species, Mycobacteria species, *Leishmania* species and *Trypanosoma* species Also provided herein are kits comprising components of a diagnostic regimen, for example components for processing a sample along with a detection assay, lateral flow device, dipstick, and instructions for using the same. The kit can also comprise packaging or a container housing at least one or more components of the diagnostic assay, and can also comprise instructions on storage, administration, dosing or the like and/or an insert regarding the active ingredients. The kit can also comprise instructions for monitoring the presence and/or prevalence of an infectious organisms (or metabolites thereof) once administered, and optionally, materials for performing such assays including, e.g., reagents, well plates, containers, markers or labels, spin columns, and the like. Other suitable components to include in kits of the disclosure will be readily apparent to one of skill in the art, taking into consideration the infectious organism to be detected, sample to be processed, and storage conditions.

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following examples have been included to provide guidance to one of ordinary skill in the art for practicing representative embodiments of the presently disclosed subject matter. In light of the present disclosure and the general level of skill in the art, those of skill can appreciate that the following examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Recombinant IntL-1 Binds to *Aspergillus* Ethanol Precipitate and Whole Cells (Conidia and Hyphae).

Method for Ethanol Precipitate binding.

Wells of a microtiter plate were coated with 10 μg/ml of EP antigen and blocked with a blocking buffer containing 0.1% BSA in IntL-ELISA buffer (20 mM HEPES pH7.4; 150 mM NaCl; 10 mM CaCl2; 0.1% Tween-20. Ref: Wesener et al. (2015) Nature Structural & Molecular Biology, 22(8):603). Recombinant human IntL-1 (rIntL-1) was serially diluted tenfold in blocking buffer starting at $10^{-6}$ M, and incubated on the EP-coated plate for 2 h at 30° C., followed by washes with IntL-ELISA buffer. The bound IntL was detected by an anti-omentin Rabbit IgG ab (Millipore) diluted 1:1000 in blocking buffer and incubated at 30° C. for 2 h. Wells were again washed and incubated with a goat anti-Rabbit IgG-AP at 1:1000 for 1 h at 30° C. Following another wash, the color was developed by AP substrate for 30 minutes at 37° C.

Method for Conidia & Hyphae Binding.

Conidia from *Aspergillus fumigatus* expressing a green fluorescent protein (GFP) were counted and adjusted to $10^6$/mL in Sabouraud's Dextrose broth, and grown for 6 hours at 37° C. to germinate (forming hyphae). The collection of swollen, germinating conidia and growing hyphae from already-germinated conidia were killed with heat at 90° C. for 1 h. The fungal material (killed conidia and hyphae) was pelleted by centrifugation, resuspended in IntL-ELISA blocking buffer, and incubated with $10^{-7}$ M rIntL-1 (FLAG-tagged) in presence of 10 μg/mL of either MAb476 or an irrelevant, isotype control antibody mouse IgM for 2 h at 30° C. Following washes with IntL-ELISA buffer, the material was resuspended in IntL-ELISA blocking buffer and incubated with a 1:50 diluted anti-FLAG tag antibody conjugated to the red fluorochrome phycoerythrin (PE). Again, after washes, the stained material was resuspended in IntL-ELISA blocking buffer, transferred to chamber slides and observed under a fluorescent microscope.

Figures 4A, 4B:
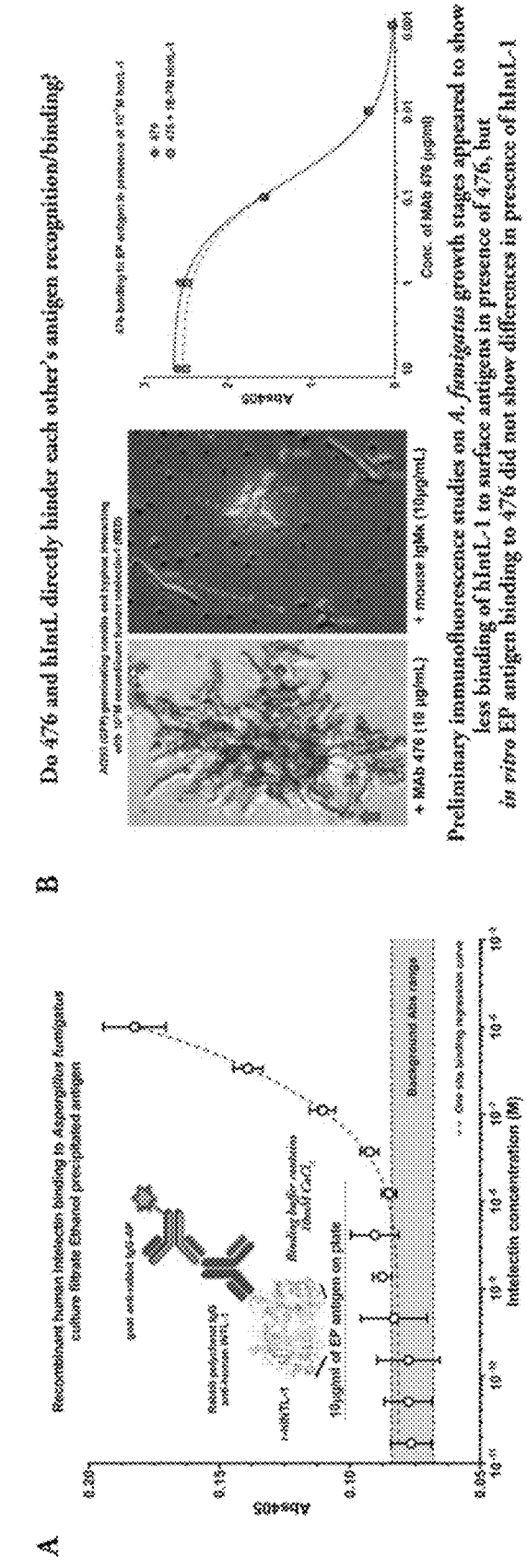
FIGS. 4A-4B depict (A) recombinant hIntL-1 binds to *Aspergillus* ethanol precipitate (EP) in an ELISA, and (B) binds to whole cells (conidia and hyphae).

The inventors performed experiments wherein *Aspergillus* ethanol precipitate and whole cells (conidia and hyphae) were exposed to rIntL-1 and then a sandwich assay using Rabbit polyclonal antibodies to hIntL and goat anti-rabbit antibodies with a fluorescent ligand were performed in buffer comprising 10 mM $CaCl_2$. As shown in FIG. 4, hIntL bound *Aspergillus* ethanol precipitate with high affinity in the presence of $Ca^{2+}$. Thus, hIntL could be the competitive agent which is interfering with the inventors' antibodies to galF.

Example 2

Human IntL-1 is Present in Human Urine.

Figure 5:
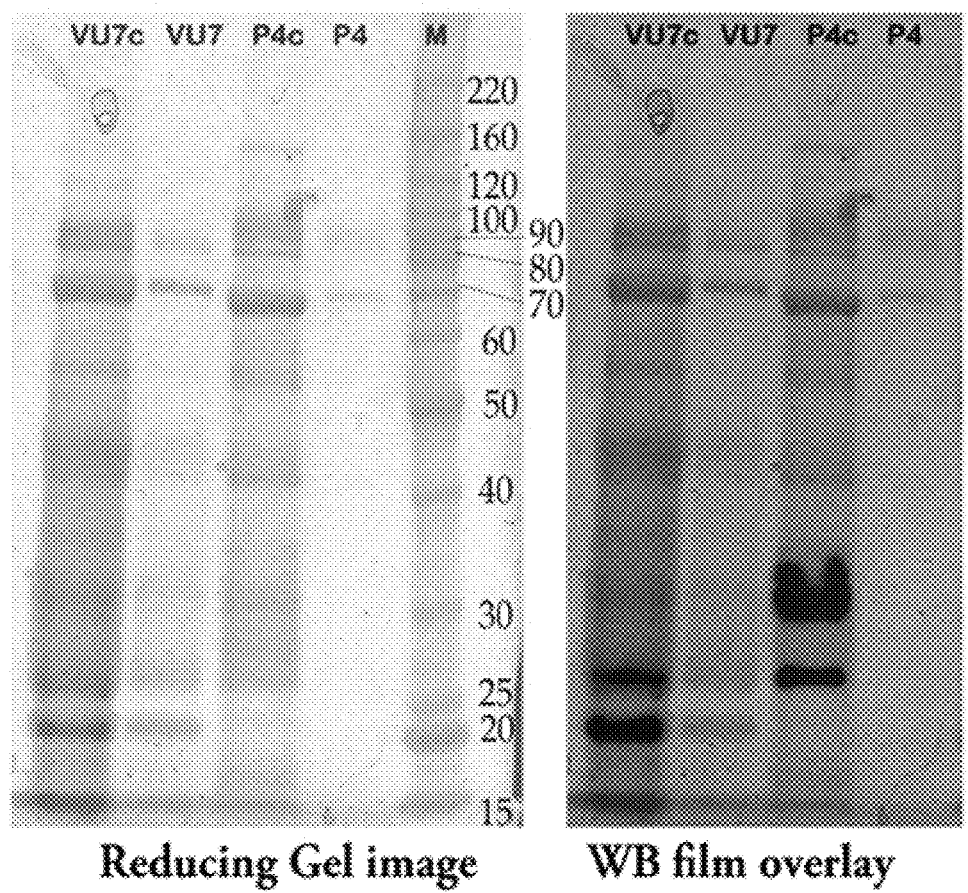
FIG. 5 shows the presence of hIntL-1 in urine from aspergillosis patient and healthy control. Bands with rabbit anti-IntL antibody seen only in lane from concentrated urine. VU7=aspergillosis patient; Pool 4/P4=healthy control urine; "c" denotes concentrated urine via Amicon (10 kDa MWCO); "ds" denotes treatment with desalting column. The gels were exposed for 5 s to SuperSignal West Pico Chemiluminescent reagent (ThermoFisher Inc.).

Studies were performed using urine collected from control patients (pool 4) and patient who had *Aspergillus* infection (VU7). The samples were run in a reducing SDS polyacrylamide gel electrophoresis (PAGE), and the resolved proteins were transferred to a nylon membrane for performing a Western Blot. Some samples used concentrated urine (denoted by "c") using an Amicon concentrator or were pretreated by desalting columns (denoted by "ds"). As expected in a reducing SDS-PAGE, IntL (homotrimer in native state) was resolved to its monomeric form (MW range ~25-40 kDa). As shown in FIG. 5, hIntL was present in patient urine and could also be detected in healthy controls in the concentrated samples.

Example 3

Patient Urine Contains a Different Form of hIntL than Healthy Urine.

Figure 6:
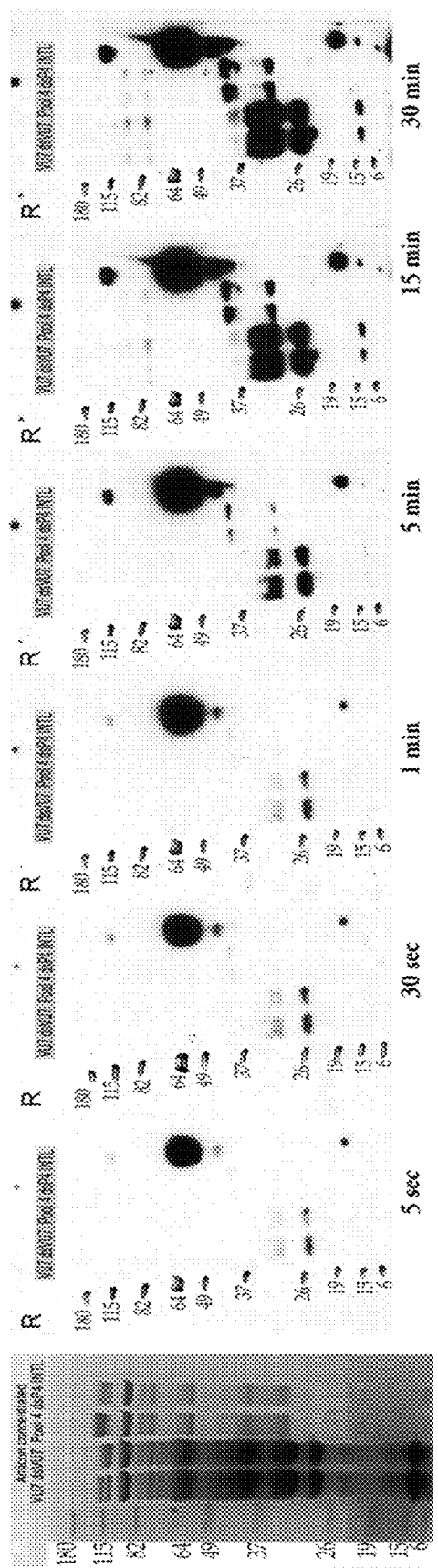
FIG. 6 shows that urine from a patient with invasive *Aspergillus* infection (aspergillosis) contains a different conformation of hIntL than healthy control urine. Radiograms from Western blots show that the aspergillosis patient urine contains small molecular weight bands which migrate at sizes consistent with subunits of the hIntL-1 heterotrimer protein. Healthy patient urine contains a single 120 kDa band of hIntL, consistent with the intact heterotrimer.
Figure 7:
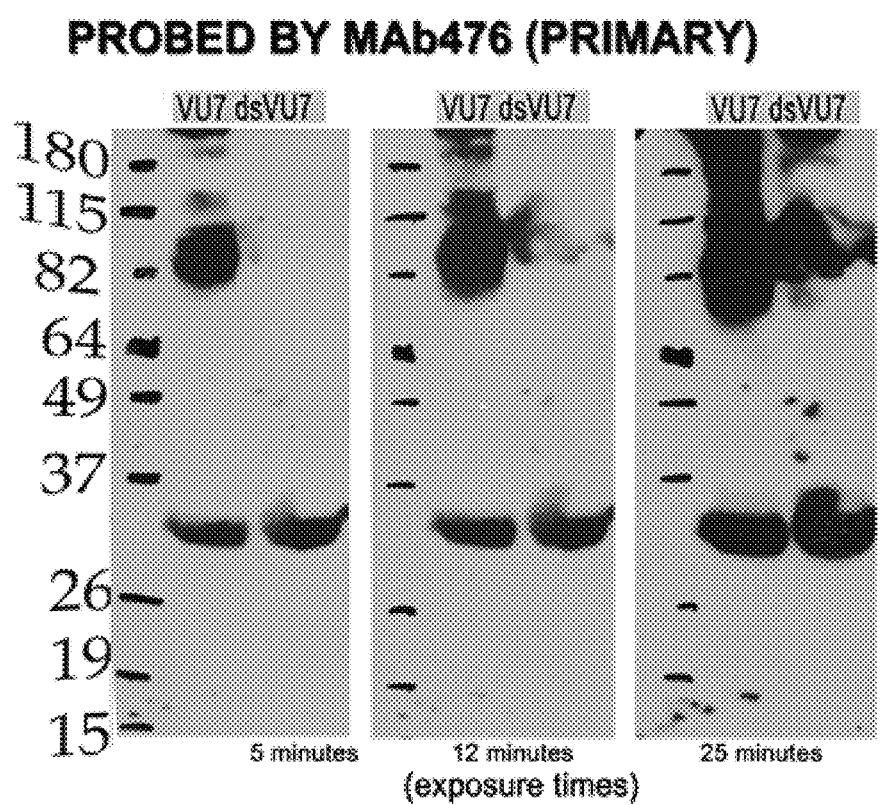
FIG. 7 shows that galF specific antibody mAB476 binds to the band that co-migrates with that recognized by anti-hIntL and shows that when the aspergillosis patient urine is desalted prior to contacting the urine with the antibody, the amount of antibody binding is increased. Desalting also appears to affect the hIntL heterotrimer protein as more of it is found in small molecular weight bands which are the subunits of hIntL.
Figure 8:
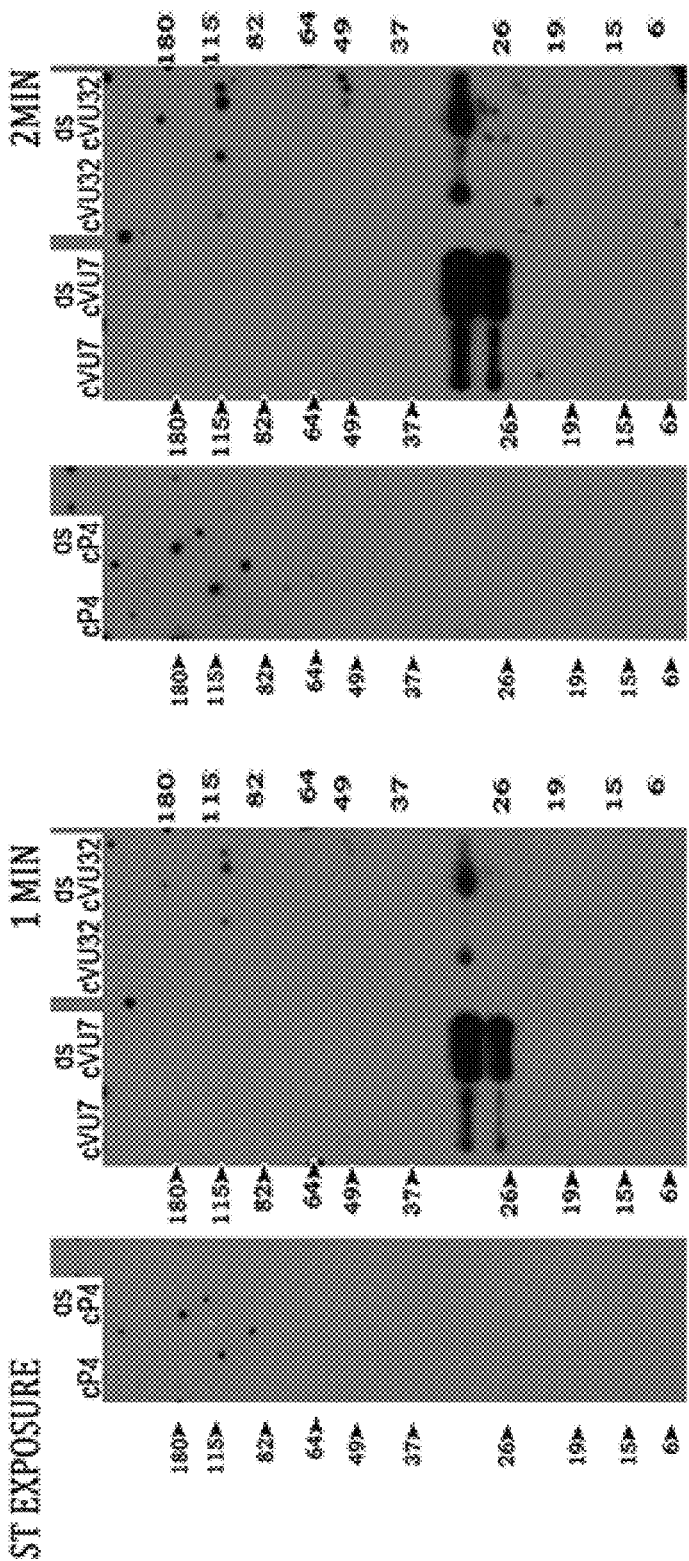
FIG. 8 depicts small to medium molecular weight proteins on SDS-PAGE gel probed with mAB476 at a 1:1000 titer and detected with goat-anti-mouse IgM-HRP at a titer of 1:10,000. The mAB476 antibody binds to these small molecular weight moieties in aspergillosis patient urine, but not in healthy patient urine; these are the galF-containing antigens that are released by the microbe.
Figure 10:
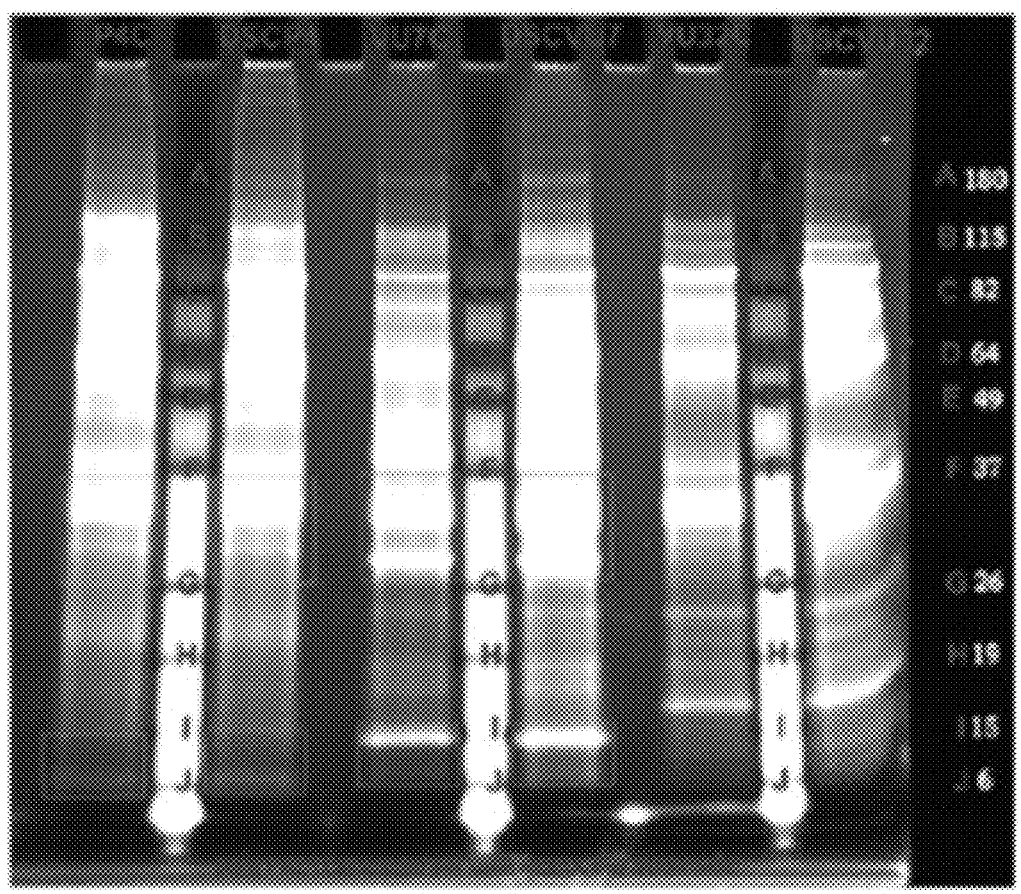
FIG. 10 depicts a reducing SDS-PAGE gels of concentrated urine from healthy (pool 4) and patient (VU7), both normal and desalted, were run and stained with Sypro-Ruby fluorescent protein stain. The small to mid-range molecular weight bands were cut out of the gels and prepared for mass spectrometry analysis.

Following up from Example 2, Western blots using enzyme-labeled Rabbit antibody to hIntL-1 along with a chemiluminescent substrate corroborate the fact that recombinant hIntL-1 is a 120 kDa homotrimer of about 40 kDa subunits, as shown by bands generated due to partial and incomplete reduction in the reducing SDS-PAGE. Monomers of native hIntL are known to vary in 25-40 kDa range. Patient urine had significantly higher concentrations (thicker bands) of small molecular weight subunits, whereas healthy urine had monomeric and dimeric subunits in the expected size range (FIG. 6).

Example 4 galF Specific Antibodies Recognize Certain Proteins in Urine.

The PEAKS search confirmed the presence of hIntL sequences in the analyzed 476-reactive eluate, indicating the increased likelihood of hIntL being the protein in the urine which competitively interferes with mAB476, and binds galF antigens.

Example 5

Testing of Various Methods to Inhibit hIntL Binding to galF Antigens in Patient Urine Samples.

Figure 11:
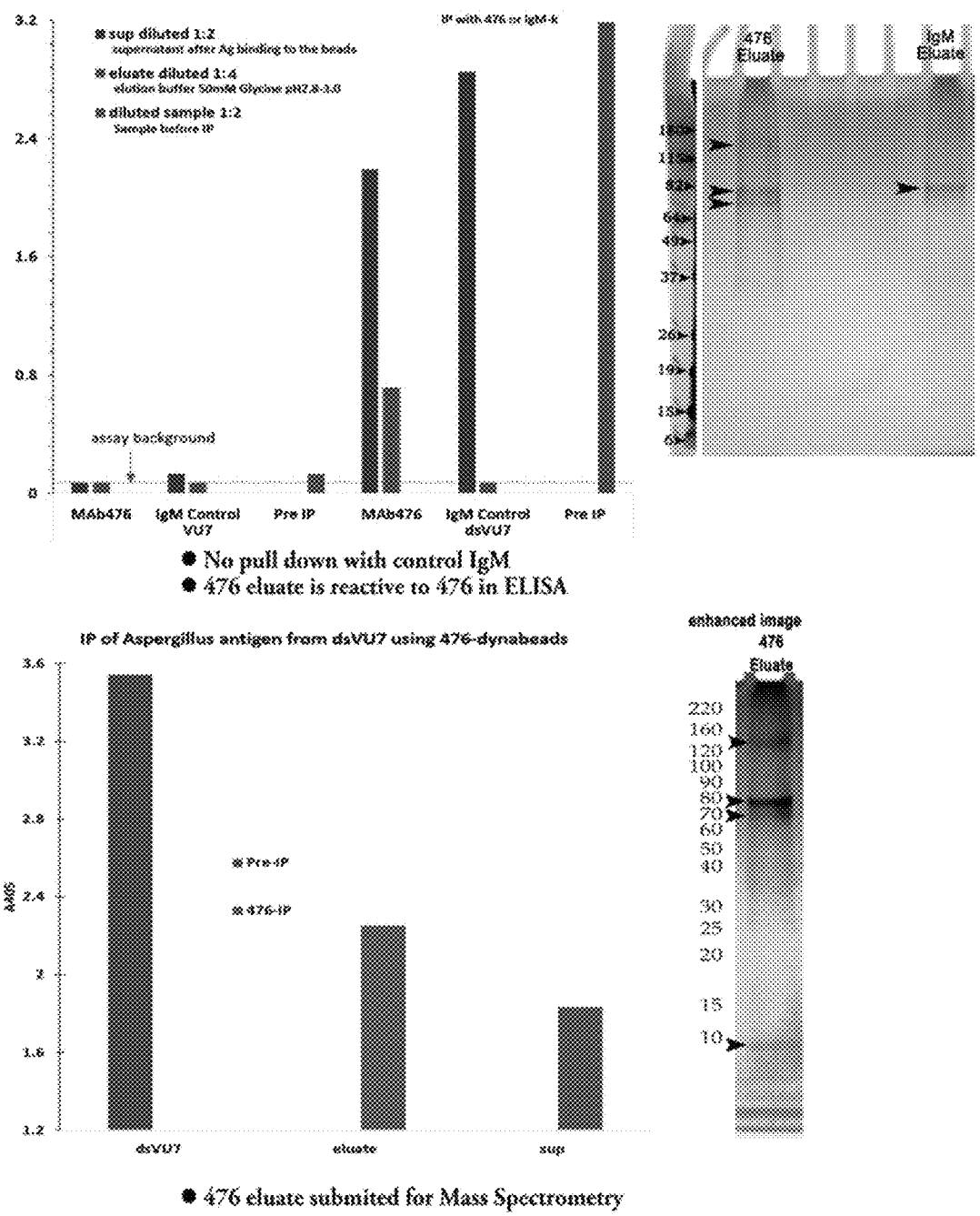
FIG. 11 shows graphs depicting immunoprecipation assays using mAB476 in urine samples of urine samples, both normal and desalted. To enrich sample detection of moieties specifically binding to mAB476, urines were incubated with superparamagnetic dynabeads coated with mAB476 and a mouse control antibody. mAB476 reactive material was eluted with 50 mM glycine (pH 2.5-3.0). No mAB476 binding occurred in normal urine. Reactivity to mAB476 eluates was confirmed by sandwich ELISA. Eluates were then run on SDS-PAGE gels to check for band patterns, and in-solution mass spectrometry analysis was performed. Analysis detected both the microbial antigen CelA/Aspf7 (a galF-containing O-glycan), and the human hIntL protein (FIG. 12).

As shown in FIG. 11, the inventors identified IntL-1 as binding to the same *Aspergillus* derived galF-bearing antigens as mAB476 antibody. Since desalting the urine samples prior to contacting the sample with the galF-reactive antibodies resulted in much greater binding and detection, it was surmised that removal of $Ca^{2+}$ in the samples caused IntL-1 to lose its native ability to bind galF, making free galF much more available to bind the galF-specific antibodies, such as mAB476. It was therefore thought, that pre-treatment of urine samples with compositions or compounds which either bound free mono and divalent cations, or which served as high-affinity hIntL-ligand, would allow the galF specific antibodies bind more of free galF in the samples.

Figure 13:
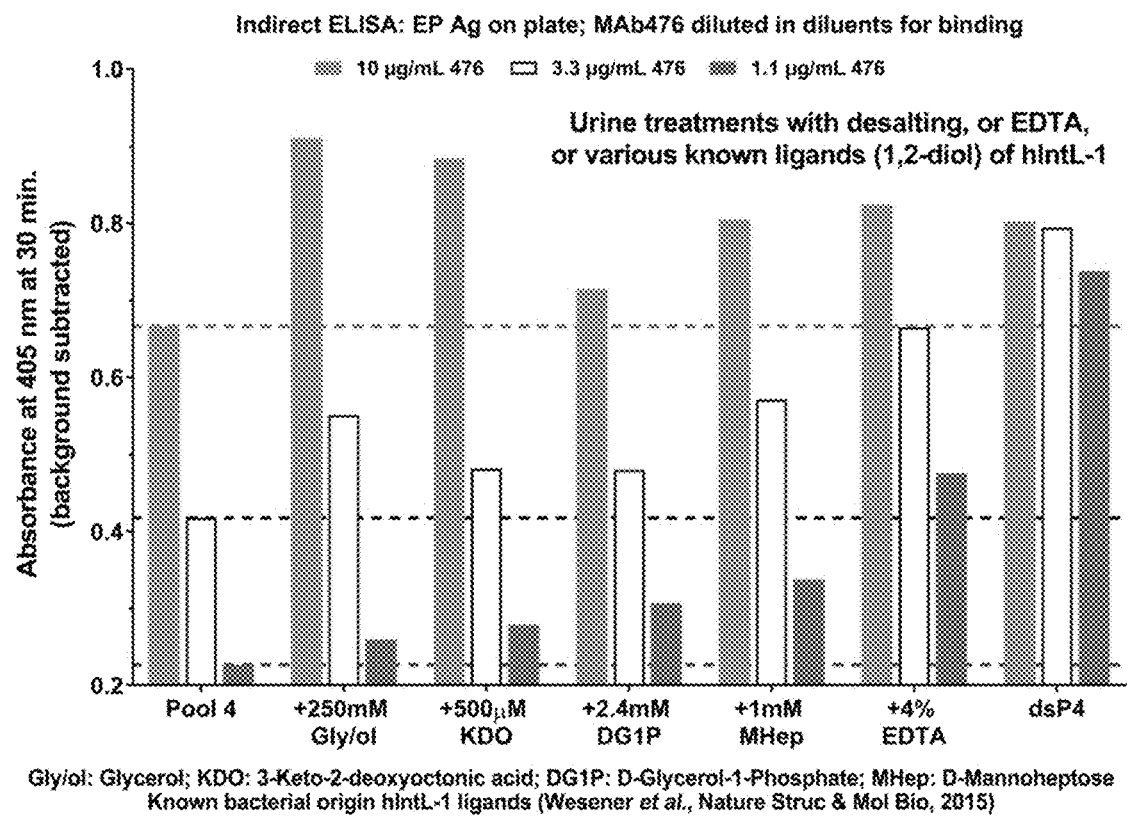
FIGS. 13 and 14 show that treatment of the patient urine with calcium chelators or other compounds which bind calcium or compete with galF for hIntL-1 binding with high affinity, when added prior to contacting the sample with galF antibodies, significantly improves detection sensitivity.

As shown in FIG. 13, in an indirect ELISA assay where *Aspergillus* ethanol precipitate containing galF is bound to the plate wells, a galF-binding antibody, such as mAB476, was added to the wells diluted in pooled healthy urine (pool 4), untreated or treated with compounds which are known hIntL ligands or $Ca^{2+}$ chelators; the samples with the known ligands or chelators had significantly greater antibody binding compared to the untreated urine, and at the highest antibody concentration, the signal was the same or better than the desalting (positive control for treatment). Thus, the inventors have developed a successful methodology to overcome hIntL competitive binding without use of extensive pretreatment processing of the urine samples.

Figure 14:
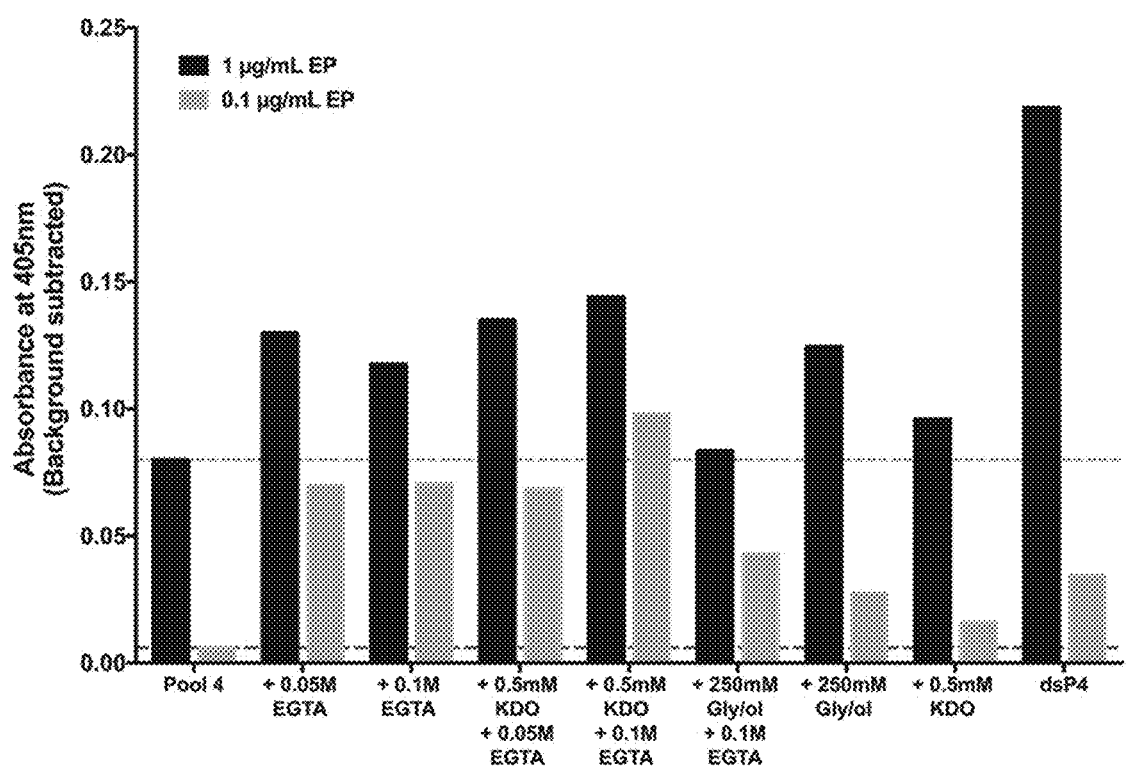

As shown in FIG. 14, in a sandwich ELISA where a galF-binding antibody, such as mAB476, is bound to the plate wells as the capture antibody, low concentrations of *Aspergillus* ethanol precipitate, namely 0.1 and 1 µg/mL, were diluted in urine, untreated or treated with compounds that are known ligands of hIntL, or $Ca^{2+}$ chelators, or a combination thereof, incubated with the same galF-binding antibody mAB476 conjugated to enzyme alkaline phosphatase (AP) as the detection reagent, and finally placed in the mAB476 coated wells. Following further incubation, the bound Ab-Ag-Ab complex was detected via color development using a substrate of AP. It was observed that the samples with the known ligands or chelators had significantly greater antibody binding signal at low antigen concentrations compared to the untreated urine sample. This recapitulates the success of the methodology developed by the inventors to circumvent the hIntL competitive binding without extensive sample pre-treatment for detection of low antigen concentrations.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for diagnosing a microbial infection in a biological sample from a mammalian subject suspected of having, having, or susceptible to having a microbial infection by detecting the presence of at least one polysaccharide comprising a galactofuranose residue in a biological sample of the mammalian subject, the method comprising:

(a) treating the biological sample to inhibit human intelectin (hIntL) binding of galactofuranose residues present in the sample, wherein the treatment of the biological sample comprises contacting the biological sample with at least one ligand which binds directly to intelectin, or substrates which bind divalent cations with high affinity;

(b) contacting the treated sample of (a) with at least one antibody specific for at least one polysaccharide comprising a galactofuranose residue in an effective amount to produce a detectable amount of antibody-polysaccharide complex, wherein the at least one antibody specific for at least polysaccharide comprising a galactofuranose residue is selected from the group consisting of monoclonal antibody 205 (MAb 205) comprising a variable heavy (VH) domain of SEQ ID NO:1 and a variable light (VL) domain of SEQ ID NO:2; monoclonal antibody 24 (MAb 24) comprising a VH domain of SEQ ID NO:3 and a VL domain of SEQ ID NO:4; monoclonal antibody 686 (MAb 686) comprising a VH domain of SEQ ID NO:5 and a VL domain of SEQ ID NO:6; monoclonal antibody 838 (MAb 838) comprising a VH domain of SEQ ID NO:7 and a VL domain of SEQ ID NO:8; and monoclonal antibody 476 (MAb 476) comprising a VH domain of SEQ ID NO:9 and a VL domain of SEQ ID NO:10; and (c) detecting the presence of at least one antibody-polysaccharide complex, wherein the detection of the presence of at least one antibody-polysaccharide complex is diagnostic of a microbial infection in a mammalian subject.

2. The method of claim 1, wherein in step (a) treating the sample comprises contacting the sample with a substrate.

3. The method of claim 2, wherein the substrate comprises a polyacrylamide resin.

4. The method of claim 2, wherein the substrate comprises a desalting column.

5. The method of claim 4, wherein the desalting column has a molecular weight cut off of less than 10 kDa.

6. The method of claim 4, wherein the desalting column has a molecular weight cut off of 7 kDa.

7. A method for optimizing an assay for detecting the presence of at least one polysaccharide comprising a galF residue in a biological sample of the mammalian subject, the method comprising:

(a) treating the biological sample comprising contacting the sample with a substrate which binds salts with high affinity, thereby inhibiting human intelectin (hIntL) binding of galF residues present in the sample;

(b) contacting the treated sample of (a) with at least one antibody specific for at least one polysaccharide comprising a galF residue in an effective amount to produce a detectable amount of antibody-polysaccharide complex, wherein the at least one antibody specific for at least polysaccharide comprising a galactofuranose residue is selected from the group consisting of monoclonal antibody 205 (MAb 205) comprising a variable heavy (VH) domain of SEQ ID NO:1 and a variable light (VL) domain of SEQ ID NO:2; monoclonal antibody 24 (MAb 24) comprising a VH domain of SEQ ID NO:3 and a VL domain of SEQ ID NO:4; monoclonal antibody 686 (MAb 686) comprising a VH domain of SEQ ID NO:5 and a VL domain of SEQ ID NO:6; monoclonal antibody 838 (MAb 838) comprising a VH domain of SEQ ID NO:7 and a VL domain of SEQ ID NO:8; and monoclonal antibody 476 (MAb 476) comprising a VH domain of SEQ ID NO:9 and a VL domain of SEQ ID NO:10; and (c) detecting the presence of at least one antibody-polysaccharide complex.

8. The method of claim 7, wherein the substrate comprises a polyacrylamide resin.

9. The method of claim 7, wherein the substrate comprises a desalting column.

10. The method of claim 9, wherein the desalting column has a molecular weight cut off of less than 10 kDa.

11. The method of claim 9, wherein the desalting column has a molecular weight cut off of 7 kDa.

* * * * *

SEQUENCE LISTING

```
<160> NUMBER OF SEQ ID NOS: 10

<210> SEQ ID NO 1
<211> LENGTH: 339
<212> TYPE: DNA
<213> ORGANISM: Artificial Sequence
<220> FEATURE:
<223> OTHER INFORMATION: Description of Artificial Sequence: Synthetic
      Murine 205 VH (15A)

<400> SEQUENCE: 1
gaggtgcagc tggaggagtc tctgagactc tcctgtgcaa cttctgggtt caccttcagt    60
```

```
gatttctaca tggagtgggt ccgccagcct ccagggaaga gactggagtg gattgctgca 120
agtagaaaca aagctaatga ttatacaaca gagtacagtg catctgtgaa gggtcggttc 180
atcgtctcca gagacacttc ccaaagcatc ctctaccttc agatgaatgc cctgagagct 240
gaggacactg ccatttatta ctgtgcaaga gattactacg gtagtagcta ctggtacttc 300
gatgtctggg gcgcagggac cacggtcacc gtctcctca 339

<210> SEQ ID NO 2
<211> LENGTH: 341
<212> TYPE: DNA
<213> ORGANISM: Artificial Sequence
<220> FEATURE:
<223> OTHER INFORMATION: Description of Artificial Sequence: Synthetic
Murine 205 VL (P1A)

<400> SEQUENCE: 2
gacattctga tgacccagtc tccaactttc cttgctgtga cagcaagtaa gaaggtcacc 60
attagttgca cggccagtga gagcctttat tcaagcaaac acaaggtgca ctacttggct 120
tggtaccaga agaaaccaga gcaatctcct aaactgctga tatacggggc atccaaccga 180
tacattgggg tccctgatcg cttcacaggc agtggatctg ggacagattt cactctgacc 240
atcagcagtg tacaggttga agacctcaca cattattact gtgcacagtt ttacagctat 300
cctctcacgt tcggctcggg gacaaagttg gaaataaaac g 341

<210> SEQ ID NO 3
<211> LENGTH: 359
<212> TYPE: DNA
<213> ORGANISM: Artificial Sequence
<220> FEATURE:
<223> OTHER INFORMATION: Description of Artificial Sequence: Synthetic
Murine 24.22.1 VH (PA7)
<220> FEATURE:
<221> NAME/KEY: modified_base
<222> LOCATION: (18)..(18)
<223> OTHER INFORMATION: a, c, g, or t

<400> SEQUENCE: 3
gaggtgcagc tggaggantc tgggggagac ttagtgaagc ctggagggtc cctgaaactc 60
```

```
tcctgtgcag cctctggatt cactttcagt agctatggca tgtcttgggt tcgccagact 120
ccagacaaga ggctggagtg ggtcgcaacc attagtagtg gtggtagtta cacctactat 180
ccagacagtg tgaaggggcg attcaccatc tccagagaca atgccaagaa caccctgtac 240
ctgcaaatga gcagtctgaa gtctgaggac acagccatgt attactgtgc aagacttact 300
acggtagtag ctatgctatg gactactggg gtcaaggaac ctcagtcacc gtctcctca 359

<210> SEQ ID NO 4
<211> LENGTH: 341
<212> TYPE: DNA
<213> ORGANISM: Artificial Sequence
<220> FEATURE:
<223> OTHER INFORMATION: Description of Artificial Sequence: Synthetic
Murine 24.22.1 VL (B6A)

<400> SEQUENCE: 4
gacattctga tgacccagtc tccaactttc cttgctgtga cagcaagtaa gaaggtcacc 60
attagttgca cggccagtga gagcctttat tcaagcaaac acaaggtgca ctacttggct 120
tggtaccaga agaaaccaga gcaatctcct aaactgctga tatacggggc atccaaccga 180
tacattgggg tccctgatcg cttcacaggc agtggatctg ggacagattt cactctgacc 240
```

```
atcagcagtg tacaggttga agacctcaca cattattact gtgcacagtt ttacagctat    300
cctctcacgt tcggtgctgg gaccaagctg gagctgaaac g                        341
```

<210> SEQ ID NO 5
<211> LENGTH: 341
<212> TYPE: DNA
<213> ORGANISM: Artificial Sequence
<220> FEATURE:
<223> OTHER INFORMATION: Description of Artificial Sequence: Synthetic
      Murine 686.8.5 VH (C5A)

<400> SEQUENCE: 5

```
gacattctga tgacccagtc tccaactttc cttgctgtga cagcaagtaa gaaggtcacc    60
attagttgca cggccagtga gagcctttat tcaagcaaac acaaggtgca ctacttggct   120
tggtaccaga agaaaccaga gcaatctcct aaactgctga tatacggggc atccaaccga   180
tacattgggg tccctgatcg cttcacaggc agtggatctg ggacagattt cactctgacc   240
atcagcagtg tacaggttga agacctcaca cattattact gtgcacagtt ttacagctat   300
cctctcacgt tcggtgctgg gaccaagctg gagctgaaac g                        341
```

<210> SEQ ID NO 6
<211> LENGTH: 341
<212> TYPE: DNA
<213> ORGANISM: Artificial Sequence
<220> FEATURE:
<223> OTHER INFORMATION: Description of Artificial Sequence: Synthetic
      Murine 686.8.5 VL (P2A)

<400> SEQUENCE: 6

```
gacattctga tgacccagtc tccaactttc cttgctgtga cagcaagtaa gaaggtcacc    60
attagttgca cggccagtga gagcctttat tcaagcaaac acaaggtgca ctacttggct   120
tggtaccaga agaaaccaga gcaatctcct aaactgctga tatacggggc atccaaccga   180
tacattgggg tccctgatcg cttcacaggc agtggatctg ggacagattt cactctgacc   240
atcagcagtg tacaggttga agacctcaca cattattact gtgcacagtt ttacagctat   300
ccgctcacgt tcggtgctgg gaccaagctg gagctgaaac g                        341
```

<210> SEQ ID NO 7
<211> LENGTH: 342
<212> TYPE: DNA
<213> ORGANISM: Artificial Sequence
<220> FEATURE:
<223> OTHER INFORMATION: Description of Artificial Sequence: Synthetic
      Murine 838.9.4 VH (B4B)

<400> SEQUENCE: 7

```
gaggtgcagc tggaggagtc tctgagactc tcctgtgcaa cttctgggtt caccttcagt    60
gatttctaca tggagtgggt ccgccagcct ccagggaaga gactggagtg gattgctgca   120
agtagaaaca aagctaatga ttatacaaca gagtacagtg catctgtgaa gggtcggttc   180
ttcgtctcca gagacacttc ccaaagcatc ctctaccttc agatgaatgc cctgagagct   240
gaggacactg ccatttatta ctgtgcaaga gatgttatga ttacgacggg ggactggtac   300
ttcgatgtct ggggcgcagg gaccacggtc accgtctcct ca                      342
```

<210> SEQ ID NO 8
<211> LENGTH: 318
<212> TYPE: DNA
<213> ORGANISM: Artificial Sequence

```
<220> FEATURE:
<223> OTHER INFORMATION: Description of Artificial Sequence: Synthetic
      Murine 838.9.4 VL (p6)

<400> SEQUENCE: 8
gacattctga tgacccagtc tcaaaaattc atgtccacat cagtaggaga cagggtcagc    60
gtcacctgca aggccagtca gaatgtgggt actaatgtag cctggtatca acagaaacca   120
gggcaatctc ctaaagcact gatttactcg gcatcctacc agtacagtgg agtccctgat   180
cgcttcacag gcagtggatc tgggacagat ttcactctca ccatcagcaa tgtgcagtct   240
gaagacttgg cagagtattt ctgtcagcaa tttaacagct atcacgttcg gctcggggac   300
aaagttggaa ttaaaacg                                                 318

<210> SEQ ID NO 9
<211> LENGTH: 375
<212> TYPE: DNA
<213> ORGANISM: Artificial Sequence
<220> FEATURE:
<223> OTHER INFORMATION: Description of Artificial Sequence: Synthetic
      Murine 476 VH (P10B-TA)

<400> SEQUENCE: 9
gaggtgcagc tggaggagtc tggaggaggc ttggtacagc ctggggggttc tctgagactc   60 tcctgtgcaa cttctgggtt caccttcagt gatttctaca tggagtgggt ccgccagact  120
ccaggggaga gactggagtg gattgctgca agtagaaaca agctaatga ttatacagca   180 gaatacagtg cgtctgtgaa gggtcgattc accgtcttta gagacacttc ccaaaacatc  240
ctctaccttc agatgaatgc cctgagagct gaagacactg ccgcctatta ctgtgcaaga  300
gatgcggact acggtaaaac cttttcctgg tacttcgatg tctggggcgc agggaccacg  360
gtcaccgtct catca                                                   375

<210> SEQ ID NO 10
<211> LENGTH: 338
<212> TYPE: DNA
<213> ORGANISM: Artificial Sequence
<220> FEATURE:
<223> OTHER INFORMATION: Description of Artificial Sequence: Synthetic
      Murine 476 VL (F6A*-TA)

<400> SEQUENCE: 10
gatattgtaa tgacccaaga tgaactctcc aatcctgtca cttctggaga atcagttcac   60
atctcctgca ggtctagtaa gagtctccta tataaggatg ggaagacata cttgaattgg  120
tttctgcaga gaccaggaca atctcctcag ctcctgatct atttgatgtc cacccgtgca  180
tcaggagtct cagaccggtt tagtggcagt gggtcaggaa cagatttcac cctggaaatc  240
agtagagtga aggctgagga tgtgggtgtg tattattgtc aacaacttgt agaatatccg  300
ctcacgttcg gtgctgggac caagctggag ctgaaacg                          338
```